(12) United States Patent
Schlegel et al.

(10) Patent No.: US 7,386,340 B2
(45) Date of Patent: *Jun. 10, 2008

(54) SYSTEM FOR THE DIAGNOSIS AND MONITORING OF CORONARY ARTERY DISEASE, ACUTE CORONARY SYNDROMES, CARDIOMYOPATHY AND OTHER CARDIAC CONDITIONS

(75) Inventors: Todd T. Schlegel, Nassau Bay, TX (US); Brian Arenare, Houston, TX (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 1010 days.

This patent is subject to a terminal disclaimer.

(21) Appl. No.: 10/402,866

(22) Filed: Mar. 26, 2003

(65) Prior Publication Data
US 2004/0039292 A1 Feb. 26, 2004

(51) Int. Cl.
*A61B 5/0452* (2006.01)
(52) U.S. Cl. ...................................... 600/517; 600/508

(58) Field of Classification Search ................ 600/509, 600/523, 508, 515, 517, 518, 521
See application file for complete search history.

(56) References Cited

U.S. PATENT DOCUMENTS

| 4,422,459 | A | | 12/1983 | Simson |
| 5,046,504 | A | | 9/1991 | Albert et al. |
| 5,117,833 | A | | 6/1992 | Albert et al. |
| 5,348,020 | A | | 9/1994 | Hutson |
| 5,655,540 | A | | 8/1997 | Seegobin |
| 5,819,741 | A | * | 10/1998 | Karlsson et al. ............ 600/523 |
| 5,954,664 | A | | 9/1999 | Seegobin |
| 6,073,046 | A | * | 6/2000 | Patel et al. ................. 600/509 |

* cited by examiner

*Primary Examiner*—George R Evanisko
(74) *Attorney, Agent, or Firm*—Theodore U. Ro

(57) ABSTRACT

Cardiac electrical data are received from a patient, manipulated to determine various useful aspects of the ECG signal, and displayed and stored in a useful form using a computer. The computer monitor displays various useful information, and in particular graphically displays various permutations of reduced amplitude zones and kurtosis that increase the rapidity and accuracy of cardiac diagnoses. New criteria for reduced amplitude zones are defined that enhance the sensitivity and specificity for detecting cardiac abnormalities.

16 Claims, 19 Drawing Sheets

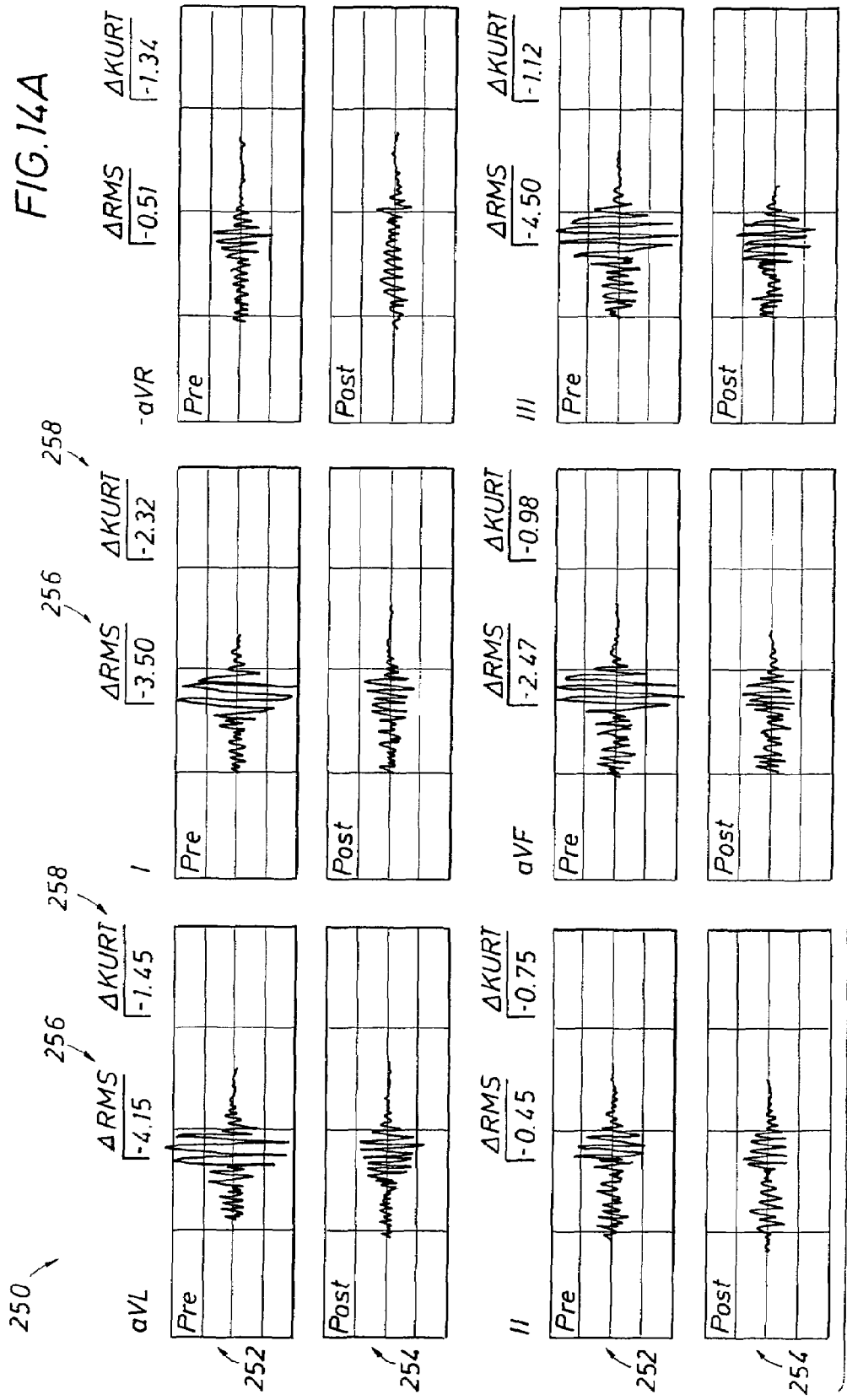

SYSTEM FOR THE DIAGNOSIS AND MONITORING OF CORONARY ARTERY DISEASE, ACUTE CORONARY SYNDROMES, CARDIOMYOPATHY AND OTHER CARDIAC CONDITIONS

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD OF THE INVENTION

The present invention relates generally to the field of electrocardiography, and more particularly to a non-invasive, real-time processing system and method to analyze, process, store, recall and display electrocardiographic signals.

BACKGROUND OF THE INVENTION

Cardiovascular disease remains the leading cause of death in North America, with more than 1.6 million myocardial infarctions (MIs) occurring annually in the United States alone. Although substantial advancement in the care of patients with ischemic heart disease has recently contributed to a 20-25% improvement in survival rate, primary preventive interventions with a similar impact on survival could, in theory, avert more than five times as many cardiovascular deaths each year. Clinicians providing preventive care for apparently healthy individuals therefore have an important opportunity to reduce the adverse impact of cardiovascular disease in the community to the extent that they can identify patients at high risk for future vascular events.

One key problem, however, is that individuals with coronary artery disease (CAD), acute coronary syndromes (ACS) and/or other cardiac conditions such as cardiomyopathy are often difficult to identify. Moreover, up to one third of life-threatening cardiovascular events occur in the absence of traditional CAD risk factors. These considerations have led researchers to seek out improved noninvasive diagnostic techniques that can better screen for and predict cardiovascular events.

Diagnosis of abnormal cardiac conditions has relied in the past on visible alterations in the P, QRS, and T-waves, i.e. portions of the electrocardiograph periodic signal. The electrocardiograph signal includes a low frequency (LF) portion and an impressed or imbedded high frequency (HF) portion, and it has been found that although the HF portion of the signal is not particularly visible, it contains information that provides greater sensitivity in determining certain abnormalities, notably myocardial ischemia and infarction and cardiomyopathy of any etiology.

The conventional surface electrocardiogram (ECG) has long been used as a diagnostic tool for detecting problems with the heart. A representative limb-lead tracing from a conventional surface ECG in a healthy subject is shown in FIG. 1. Although the conventional ECG is useful, a significant percentage of individuals presenting to a hospital emergency room with an actual heart attack will nonetheless have a normal 12-lead conventional ECG. In addition, the conventional ECG accurately reflects only the predominant LF electrical activity of the heart, as illustrated in FIG. 1. It tells the clinician little or nothing about the less predominant (lower amplitude) HF components of the heart's electrical signal embedded within the various lower-frequency waves of the conventional ECG.

As shown in FIG. 1, the graphic representation of signals that constitute the conventional tracing is limited to visible frequencies of about 100 Hz and lower. On the other hand, higher component frequencies are known to exist within the ECG signal, but are not visible to interpreting clinicians possessing only conventional ECG equipment. To accurately detect the HFs (especially those in the important 150-250 Hz range), digital sampling rates that exceed those of most conventional ECG manufacturers are first required. Traditionally, a clinician looks for changes in the ST segments of conventional LF ECG tracings as a potential evidence for myocardial ischemia. However, during actual ischemia, diminution of the HF components within the QRS complex has been shown to occur well prior to any changes in the conventional ST segments. Thus, the visualization of HF changes within the entire QRS complex represents potentially a much more sensitive way to non-invasively detect myocardial ischemia in contrast to current conventional ECG techniques.

From off-line studies, it is known that a diminution of the amplitude of the HF components within the central portion of the QRS complex of the ECG can be a highly sensitive indicator for the presence of myocardial ischemia, myocardial infarction, or cardiomyopathy, more sensitive, for example, than changes in the ST segment of the conventional ECG. However, until now, there has been no device capable of displaying, in real time, changes in these HF QRS components in the monitored patient. While academic software programs have been designed that analyze the central HF QRS components, all such programs involve laborious off-line calculations and post-processing, and therefore have little if any clinical utility, being strictly research tools.

Thus, there remains a need for a system and method that analyzes HF components over the entire QRS interval in real time for usefulness in the clinical environment. Such a system should perform, in real time, all of the complex digital sampling, averaging, and filtering that is required to generate HF QRS ECG signals. The system should also thereafter update these HF QRS ECG signals, as well as other derived parameters, in real time on a beat-to-beat basis, supplementing the diagnostic information being obtained from the conventional (i.e. low frequency) ECG complexes at the same time.

The HF signals in the central portion of the QRS ECG complex that have generated the most research interest in terms of off-line detection of ischemia and infarction are those signals in the range of 150 to 250 Hz. The raw, analog ECG signal is typically sampled at $\geq 500$ samples per second (to digitize the signal) in order to adequately satisfy the Nyquist rate of sampling at at least twice the highest frequency of interest and in order to retain the information in the signal without loss. In the past, the sampled data have been stored, and then later processed to provide potentially useful information to the researcher.

On the other hand, Simpson, in U.S. Pat. No. 4,422,459, teaches a system which analyzes only the late portion of the QRS interval and early portion of the ST segment, and in an off-line fashion (i.e. from previously stored data) to indicate cardiac abnormalities, in particular the propensity for cardiac arrhythmia. The late portion of a post-MI patient's QRS waveform can contain a broader range (40-250 Hz) HF signal tail potentially indicative of a tendency toward ventricular tachycardia. The system in Simpson digitally processes and filters a patient's QRS signals in a reverse time manner to isolate the HF tail and avoid the filter ringing which would otherwise hide the signal. Thus, in order to do so, Simpson presupposes that the data are stored so that they can be processed in reverse time order.

Albert et al., U.S. Pat. No. 5,117,833, partially focuses on analyzing signals within the mid-portion of the QRS interval for the indication of cardiac abnormality. The system of Albert et al. uses a known technique of building up data points to derive an average of heartbeat characteristics in order to enhance signal to noise ratio. Data are collected and filtered and then stored for subsequent analysis. Thus, the system does not teach a cardiac monitor which provides the data analysis immediately from the data derived from a patient, i.e. in "real-time".

Albert et al., U.S. Pat. No. 5,046,504, similarly teaches the acquisition of QRS data and subsequent analysis. Routine calculations are performed from the data previously calculated and stored. Further, this system teaches producing a set of digital spectrum values representative of an approximate power density spectrum at each of a large number of generally equally spaced sampling time intervals of the ECG waveform.

Seegobin, in U.S. Pat. Nos. 5,655,540 and 5,954,664, provides a method for identifying CAD. The method relies on a database of various frequency ECG data taken from known healthy and diseased subjects. Comparison of the data has led to a "Score" component, indicating deviation of a patient's data from the norm. This reference is rather calculation intensive, relies strictly on signal amplitudes rather than signal morphologies, and does not suggest monitoring the condition of a patient, but rather is utilized as an off-line diagnostic tool.

Hutson, U.S. Pat. No. 5,348,020, teaches a technique of near real-time analysis and display. The technique includes inputting ECG data from multiple, sequential time intervals and formatting those data into a two-dimensional matrix. The matrix is then decomposed to obtain corresponding singular values and vectors for data compression. The compressed form of the matrix is analyzed and filtered to identify and enhance ECG signal components of interest. As with other systems, this reference focuses on late potentials, a fraction of the QRS interval, as the tool to identify cardiac disease.

Finally, *High-Frequency Electrocardiogram Analysis of the Entire QRS in the Diagnosis and Assessment of Coronary Artery Disease* by Abboud (*Progress in Cardiovascular Diseases,* Vol. XXXV, No. 5 (March/April), 1993: pp 311-328) teaches the concept of "reduced amplitude zone" (RAZ) as a diagnostic tool. However, this reference also uses post-processing, and provides no teaching of a real-time analysis system. In the disclosure to follow, the reduced amplitude zone as defined in this work may be referred to as $RAZ_A$. Further, Abboud et al. used only three of the standard 12 ECG lead positions (specifically leads V3, V4 and V5) and defined a positive test for CAD as one in which a $RAZ_A$ was present in at least two of these three selected precordial leads. Using a group of cardiac-catheterized patients who had presented with chest pain but with a normal conventional 12-lead ECG, the sensitivity and specificity of this 3 precordial-lead HF QRS ECG test for identifying significant CAD (i.e., >50% stenosis in a major coronary artery) were 75% and 80%, respectively.

Thus, there remains a need for an electrocardiograph that analyzes, in real time, the HF components of the entire QRS complex in order to provide an effective monitor for patients with possible cardiac abnormalities. Further, there remains a need for an electrocardiograph that receives the analysis of the HF components of the QRS in more than three leads (preferably in 12 or more) and automatically and sensitively provides a clear and substantially unambiguous indication of cardiac abnormalities. The present invention is directed to such an electrocardiograph.

SUMMARY OF THE INVENTION

The present invention addresses these and other needs in the art by providing automatic searches for local maxima and minima of the QRS envelope according to known RAZ criteria and separately according to three additional sets of RAZ criteria. The additional RAZ criteria improve the overall sensitivity and specificity of detecting CAD, ACS and other heart conditions such as cardiomyopathy using 12-lead HF QRS electrocardiography. The present invention further provides a real time display of various aspects of the QRS complex, including a real-time diagnosis of cardiac abnormalities according to the complete set of RAZ criteria. The invention also provides a system for such a display, and a method of displaying such aspects. The present invention further parses the HF components of the QRS complex and combines spatially related indicators from these data to more definitively indicate to the clinician the presence of cardiac abnormalities in the patient. The present invention also provides a novel display of the related indicators.

The present invention advances the state of the art by taking HF QRS electrocardiographic data immediately as they are sensed from a patient, manipulating the data in conjunction with the conventional ECG signals, and displaying the HF data in real time in a useful form on a computer screen or monitor. In one aspect, the invention displays the HF data from the QRS complex in microvolts adjacent to a display of the conventional ECG data in millivolts.

In another aspect of the invention, the HF data are analyzed with software algorithms to determine the presence or absence of RAZs. The given RAZ, of which there are at least four possible variations (i.e., the "Abboud" RAZ ($RAZ_A$), "Abboud Percent" RAZ ($RAZ_{AP}$), "NASA" RAZ ($RAZ_N$) and the "Kurtosis" RAZ ($RAZ_K$), all described below), is displayed as a real-time "go, no-go" signal on the screen. Finally, in still another aspect of the invention, not only the presence or absence any one of the four variations of RAZs, but various relations between those RAZs are determined to provide a more reliable, immediately visible indication of possible CAD or other cardiac abnormalities.

These and other features of the invention will be apparent to those of skill in the art from a review of the following detailed description along with the accompanying drawings.

DETAILED DESCRIPTION OF PREFERRED EMBODIMENTS

To summarize the present invention, in order to visualize HF QRS components of ECG signals, the following general steps are taken using the system of this invention: First, using PC-based ECG hardware and software, properly amplified ECG signals are acquired at sampling rates (preferably $\geq 1000$ samples per second) that are higher than the sampling rates used in most traditional digital ECG devices (which are typically $\leq 250\text{-}500$ samples/s). Next, the amplified incoming QRS complexes are signal-averaged in each receiving channel in order to improve the signal-to-noise ratio. Premature complexes and noisy beats are automatically eliminated (i.e., not added to the running template) by a cross correlation function that rejects any individual beat that is not adequately cross-correlated to the existing template(s). A cross correlation of at least 97% between the incoming beats in each channel and the templates in each channel is commonly defined as "adequate", but this setting is user-adjustable. The averaged complexes are then band-pass-filtered, preferably in software, using a digital filter that passes-frequencies only from 150 to 250 Hz. An example of an averaged filtered (150-250 Hz) HF QRS limb lead signal from a healthy subject is shown in FIG. 2. The amplitude of the signal components in FIG. 2 is in microvolts, whereas the scale of the trace illustrated in FIG. 1 is measured in millivolts.

Figure 1:
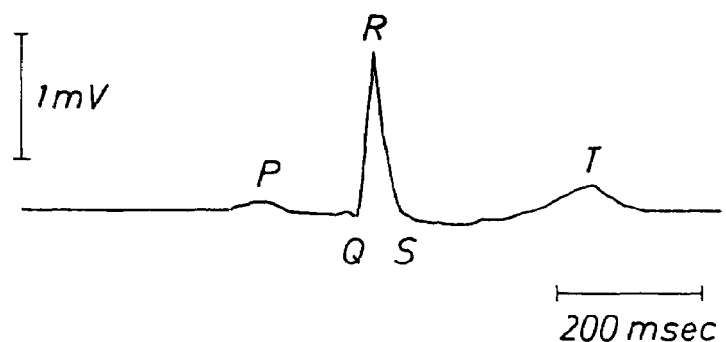
FIG. 1 is a trace of a conventional surface ECG in which only LF components are clearly visible.
Figure 2:
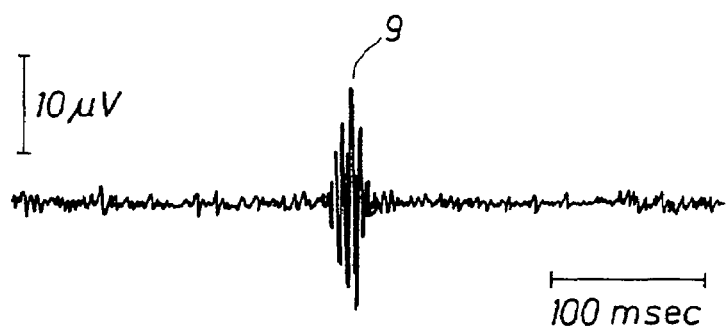
FIG. 2 is a trace of an averaged filtered (150-250 Hz) HF QRS limb lead signal from a healthy subject.
Figure 3:
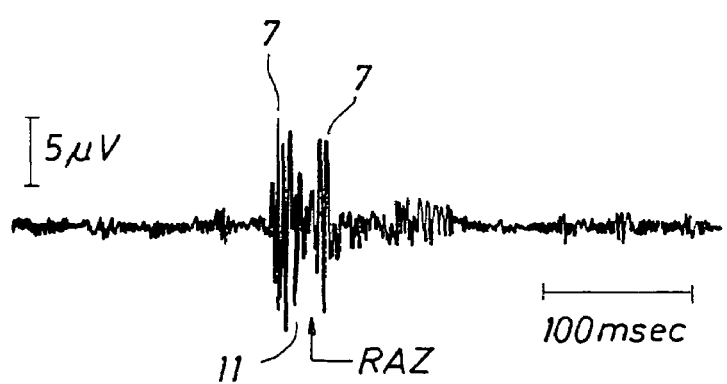
FIG. 3 is a trace of an HF QRS signal from the same lead, but in a patient with myocardial ischemia.

Thus, comparing the traces of FIGS. 1 and 2, it is apparent that the visible waveform typically offered to the clinician of the LF components hides the HF components of the QRS waveform, including valuable data regarding cardiac disease. For example, FIG. 3 shows an HF QRS signal from the same lead as that of FIG. 2, but in a patient with myocardial ischemia. Note the reduced voltage scale in FIG. 3 (compared to FIG. 2), as well as the fact that there are two peaks 7 in the envelope of the HF QRS signal rather than a single peak 9 in FIG. 2. A dip 11 in the envelope as indicated in FIG. 3 is denoted as a reduced amplitude zone (RAZ).

A RAZ classically occurs when at least two local maxima of the upper envelope or two local minima of the lower envelope are present within the HF QRS signal. A local maximum or minimum is in turn defined as an envelope sample point (peak or trough) within the QRS interval wherein the absolute value of its voltage exceeds that of the three envelope sample peaks immediately preceding and following it. The RAZ is thus the region lying between the two neighboring maxima or minima. The system of the present invention automatically searches for local maxima and minima of the QRS envelope, not only according to known off-line criteria (i.e., "$RAZ_A$"), but also separately according to three additional sets of RAZ criteria that improve the overall sensitivity and specificity for detecting CAD, ACS and other heart conditions using 12-lead HF QRS electrocardiography, as described in detail below. First, however, the basic system for the detection of RAZ and other criteria indicative of cardiac abnormalities is described below.

Basic System

Figure 4:
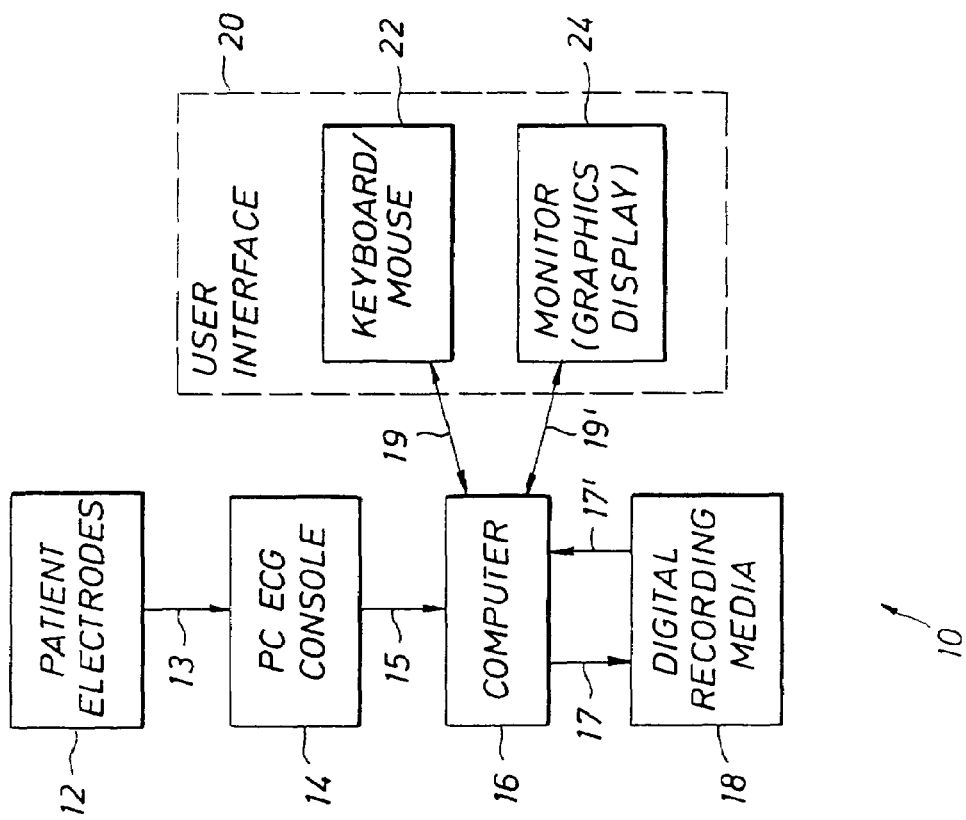
FIG. 4 is a schematic diagram of the overall system of this invention.

FIG. 4 shows a simplified, functional, block diagram of a real-time HF QRS electrocardiograph 10 constructed in accordance with the present invention. The invention monitors the cardiac function of a patient with a plurality of patient electrodes 12. The electrodes provide measurements of cardiac electrical function at various contact points on the skin of a patient in the conventional manner. For example, in the conventional 12-lead configuration, 10 electrodes placed upon the skin of the patient in the conventional configuration result in eight channels of incoming data. These eight channels are in turn translated into 12 leads of data on the patient monitor inasmuch as data for one of the bipolar limb leads and for all of the augmented unipolar limb leads can be derived if data for any two of the bipolar limb leads are already known. The analog measurements are coupled to a console 14 by way of a communications channel such as for example a cable 13. The console components are shown in greater detail in FIG. 5.

The console 14 conditions and digitizes the analog signal and provides the digitized signal to a computer 16 by way of a communications channel 15, which may preferably be a conventional cable or a wireless communication channel by radio frequency wave. The structure and function of the computer is shown and described below in respect of FIG. 6. The computer 16 is programmed to display the ECG signal in real time, although the ECG signal may also be stored on a digital recording medium 18 over a communications channel 17 for later display over a communications channel 17'.

The computer 16 is coupled to a user interface 20 which preferably includes communications devices 22 such as a mouse, keyboard, and/or touch screen. The user interface further includes a monitor 24 for user controllable graphic display of the ECG and various aspects of the signal, a feature of the present invention. The computer 16 is coupled to the interface 20 by way of bidirectional communications channels 19 and 19', for example. The aspects of the graphical display are shown in greater detail and described below in respect of FIGS. 7 through 23.

Figure 5:
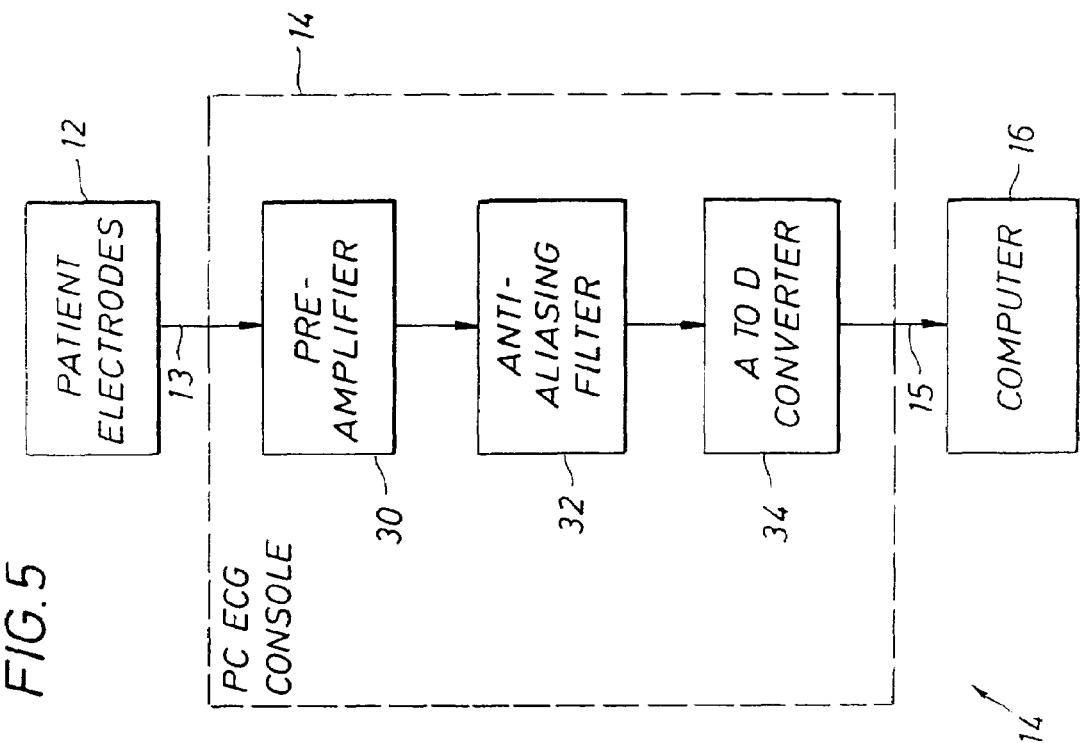
FIG. 5 is a schematic diagram of a detail of FIG. 4.

FIG. 5 depicts the structure of the console 14 in greater detail. As previously described, the patient is wired with a set of electrodes 12, such as for example a conventional set of ten electrodes for a 12-lead electrocardiograph to monitor cardiac function from different aspects of the patient's body. The electrodes 12 provide a set of analog electrical signals to the console 14, where the signals are received by a pre-amplifier 30 to boost their amplitude. The amplified signals are then fed to an anti-aliasing filter 32 having an appropriately high low-pass characteristic. The filtered signals are then fed to an analog to digital converter 34, where the signals are digitized at at least the Nyquist rate, preferably 1,000 Hz or greater, to retain all of the information contained in the analog signals. The sampled/digitized signals are then sent to the computer 16 by an appropriate medium 15.

Figure 6:
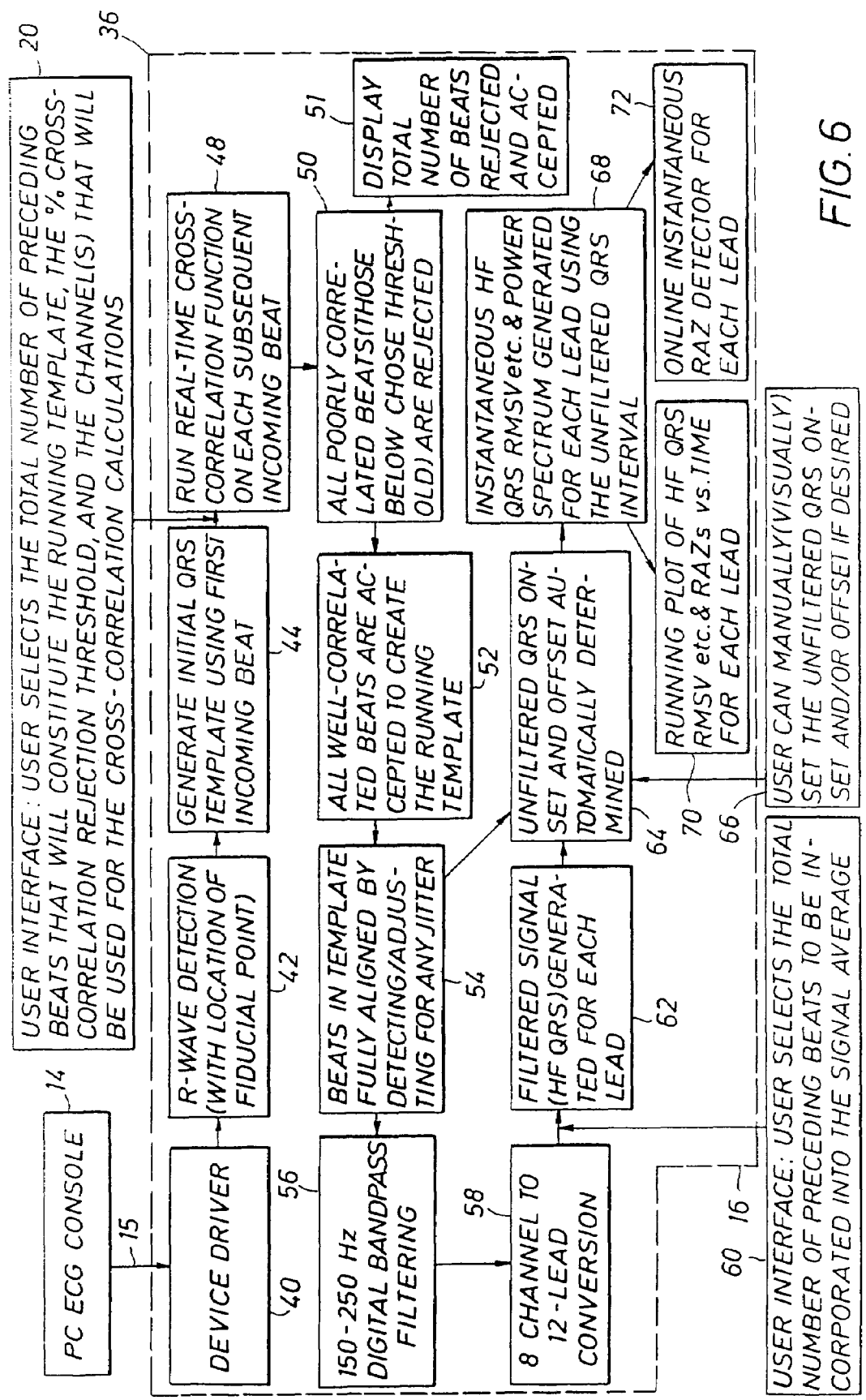
FIG. 6 is a schematic diagram of the logic carried out by a basic system, prior to the addition of the present invention.

The operation of the computer 16 is depicted in FIG. 6. The console 14 feeds the digitized ECG signals to the computer via a communications channel 15, as previously described. The computer 16 also interfaces with the user interface 20. The computer 16 receives the ECG signals into a device driver 40, which is simply the interface device and program for the console and computer. The device driver 40 provides the ECG signals in parallel to an R-wave detection block 42 to synchronize the system for the start of each heartbeat by locating the fiducial point. The following requirements must be met for temporal averaging to work effectively. First, the signal of interest must be repetitive and relatively invariable. Time varying signals, such as ectopic or premature complexes, are eliminated before averaging by comparing incoming signals against previously established templates through the use of a real-time cross-correlating technique. Second, the signal of interest must be timelocked to a fiducial point, such as near the peak of the QRS complex, that is easily detectable and serves as a timing reference for the averaging algorithm. If the signal of interest does not have a fixed, temporal relationship with the timing reference point, the resultant averaged signal will be filtered and distorted due to reference jitter, with subsequent loss of the HF components. Third, the signal of interest and the noise must be independent and remain independent during averaging.

Once the fiducial point has been located for each incoming beat, the digitized signals are fed to block 44 where initial templates of the QRS complexes are generated. The present invention includes running signal averages of the QRS complexes that constitute templates in each lead, with the number of individual beats in the running templates being selectable by the user on the user interface 20. The user can also determine the percent of cross-correlation between each new incoming beat and the templates which will be detected as a departure from the norm, and which channel(s) that will be used for the cross-correlation functions.

With the user-selected inputs as just described, the system in block 48 runs a real-time cross-correlation function on each subsequent incoming beat. In block 50, those beats which are below the threshold set by the user (or set by the system default) are rejected, with block 52 accepting only well-correlated beats to create the running templates. This feature helps to eliminate noisy, unreliable waveforms when creating the running templates. From this block, the user interface displays a continuously updated running total of the number of beats accepted and rejected in block 51, a feature of the invention.

Block 54 then aligns the beats in each channel by detecting and adjusting for any signal jitter, which may be created by any number of well-known factors, including minor inconsistencies in the detection of the fiducial point, movement by the patient or even respiration by the patient. The aligned, jitter-corrected waveforms are then fed to block 56, a band-pass filter, preferably 150-250 Hz, to select only the frequencies of interest in the waveform. Finally, the band-pass signals are fed to block 58, where, in the present embodiment, the eight channel to 12-lead conversion is performed.

From this point in the diagram of FIG. 6, blocks 62, 64, 68, 70, and 72 describe data which are displayed on the user interface 20, as shown in FIGS. 7 through 23. Block 62 shows the instantaneous, real-time filtered HF QRS signal for each lead, updating with each new beat as that beat is incorporated into the average beat. Beats that are poorly cross-correlated are rejected and thus the template averages and the display will not be altered by such beats. The display is shown by element number 114 in FIG. 7.

Figure 7:
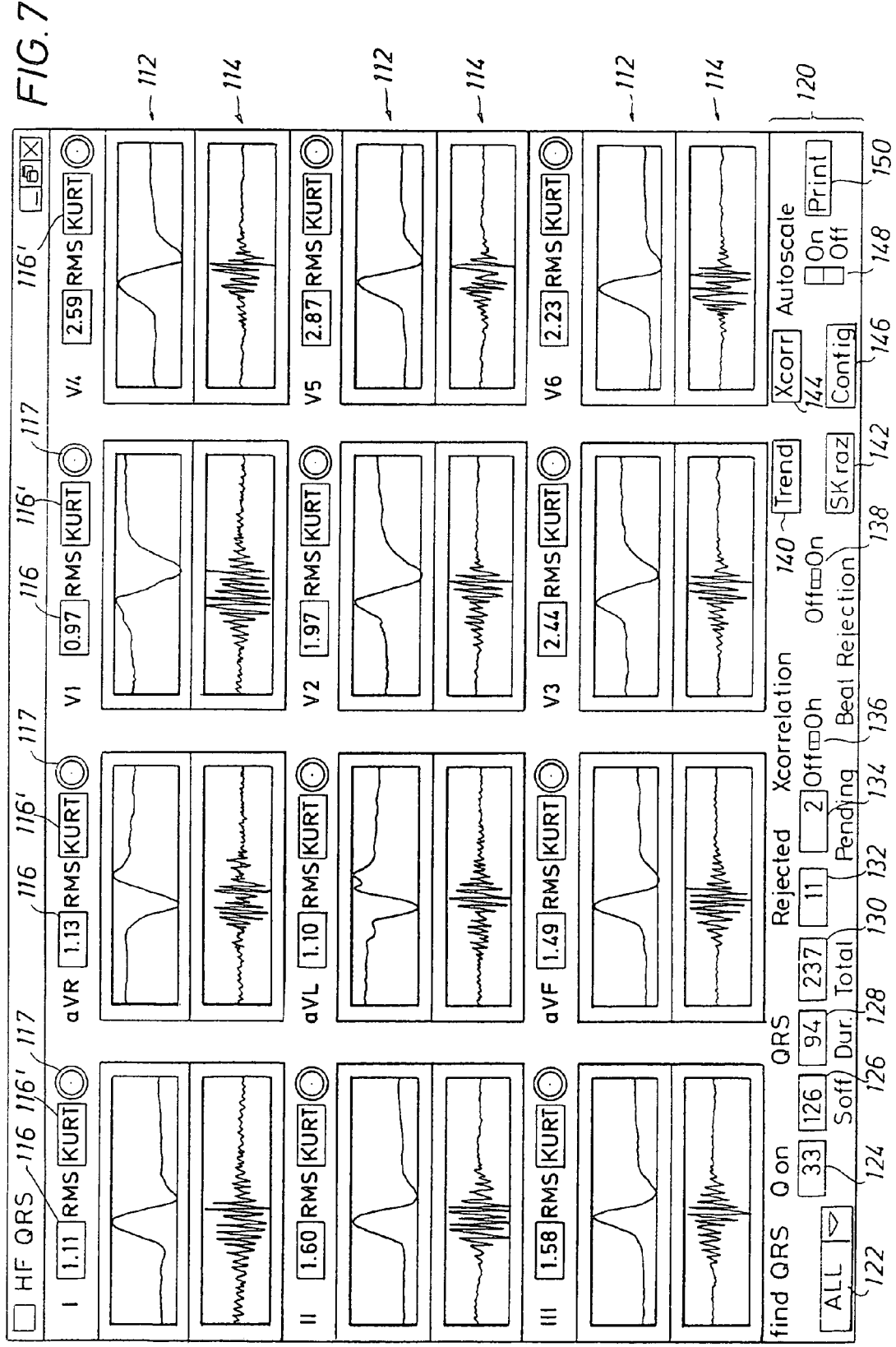
FIG. 7 is a real-time screen display, showing characteristic data obtained from a healthy subject, including a side-by-side display of a standard ECG and a filtered (HF) ECG.
Figure 11:
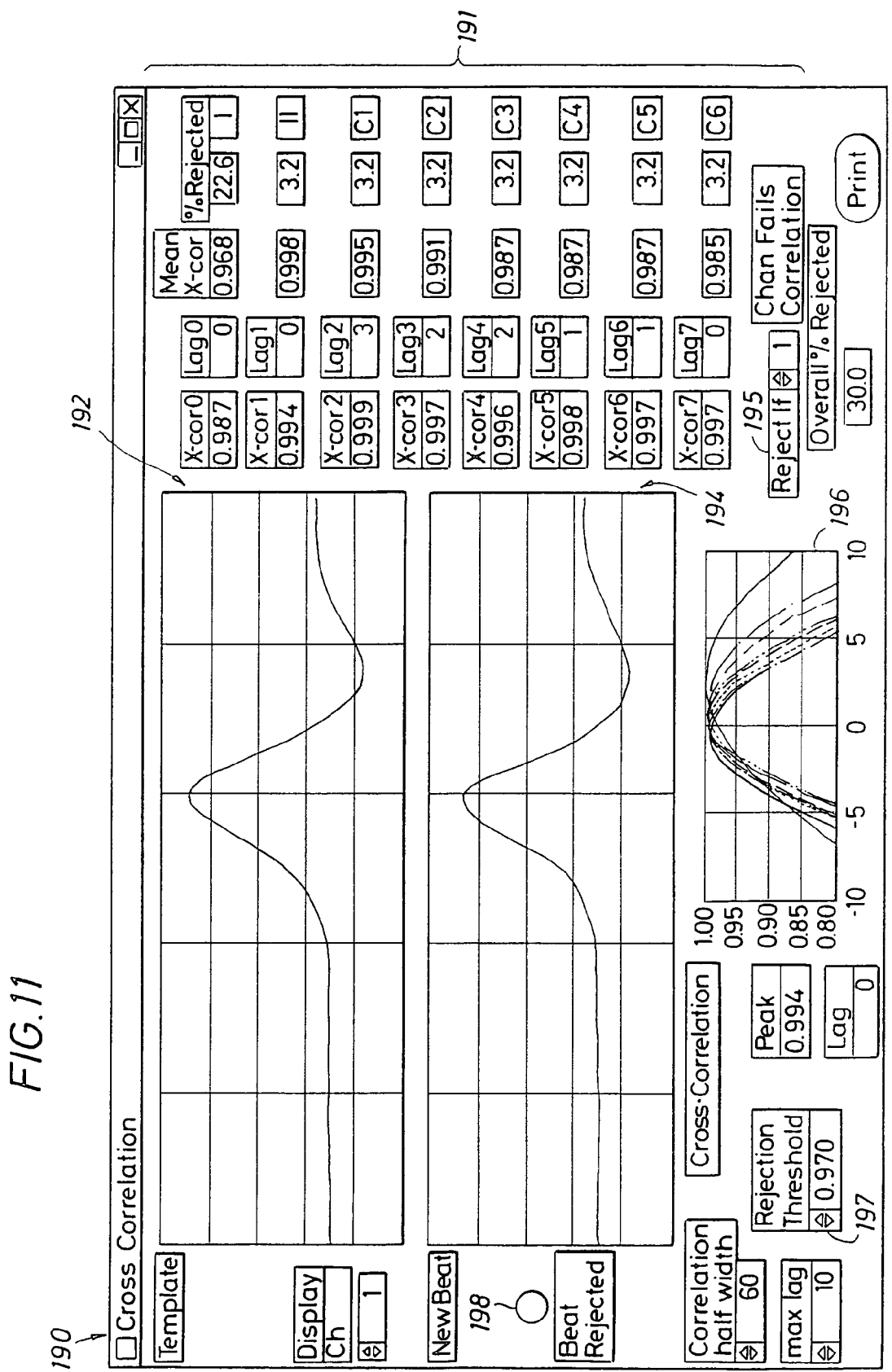
FIGS. 11 and 12 are real-time screen displays of cross correlation between a running, continuously updated signal averaged waveform, or template, and a sensed waveform to determine departure from the template from one heartbeat to the next.
Figure 12:
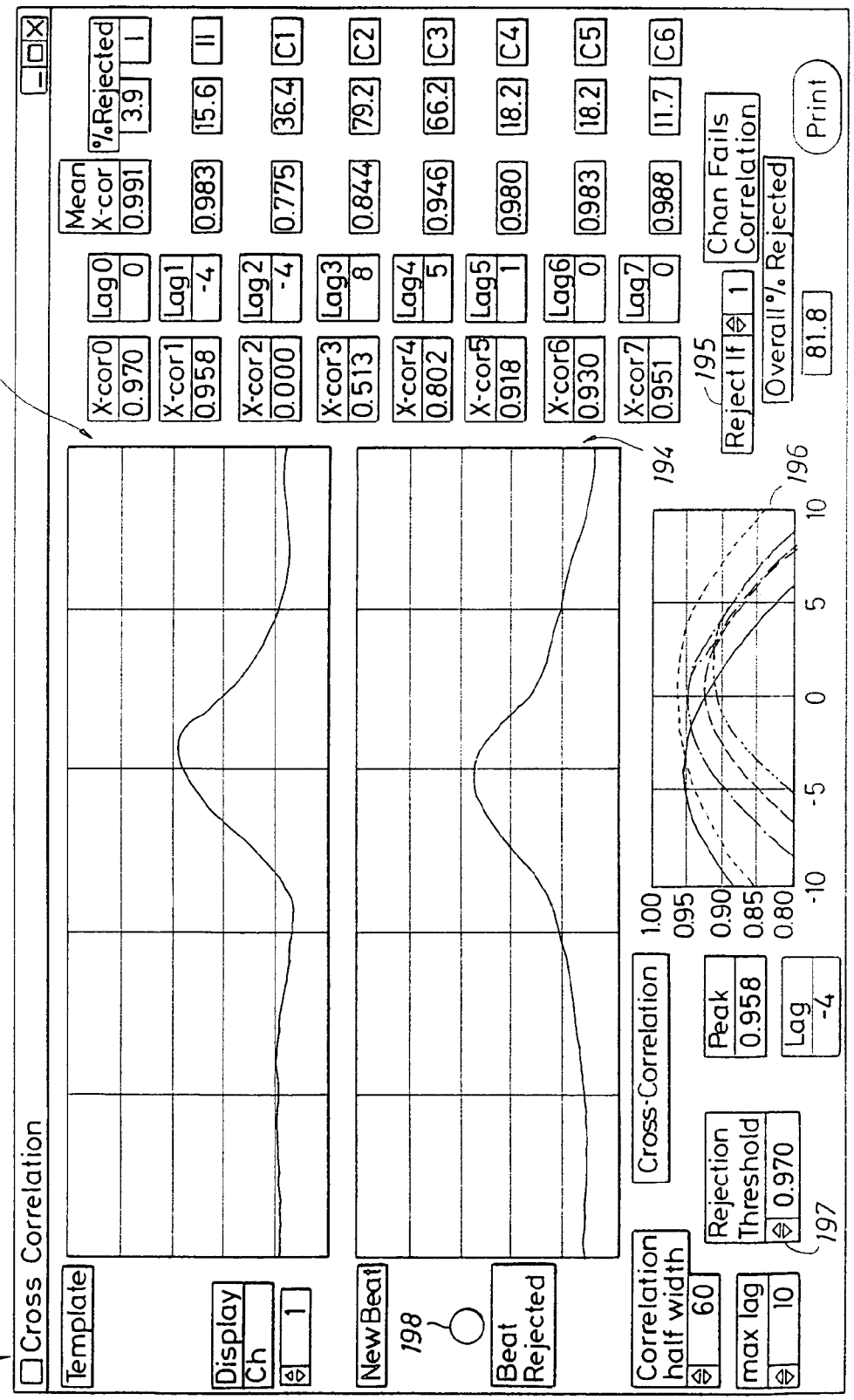

Block 64 determines the unfiltered QRS interval onset and offset automatically and in real time. This block receives an input from block 54 which detected and adjusted for any jitter in the well cross-correlated beats. The cross-correlation and jitter-correction from block 54 are therefore also displayed on the user interface, as shown in FIGS. 11 and 12. Block 68 describes the display of certain instantaneous measures of HF QRS amplitude, including the root mean square (RMS) voltage, the high frequency energy (HFQE) and the high frequency integral of absolute value (HFAV) generated for each lead using the unfiltered QRS interval onset and offset. The measures of amplitude are mathematically defined hereinafter, whereas the unfiltered QRS interval onset and offset are shown in FIG. 7 as element numbers 116 and 128, respectively.

Figure 13:
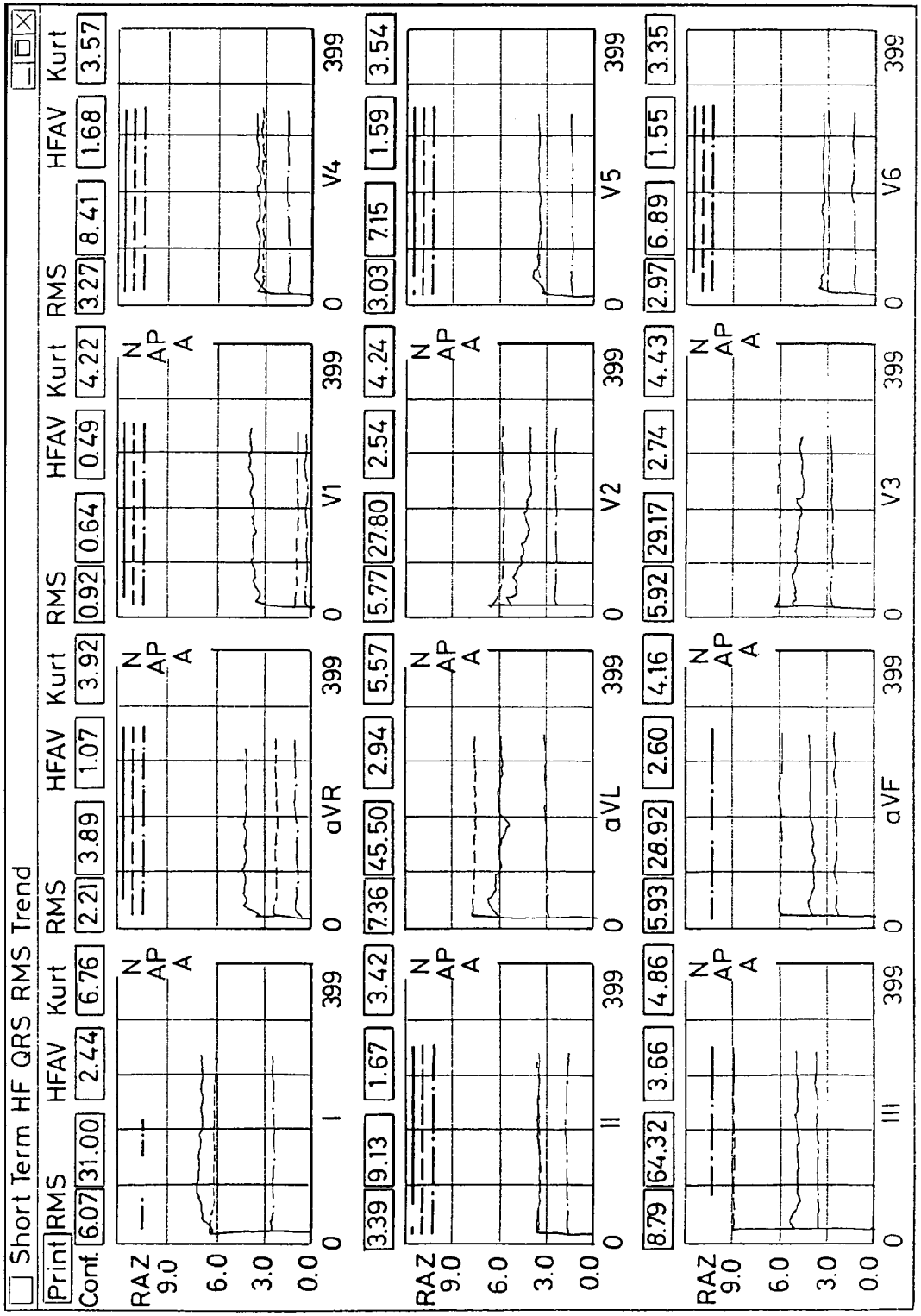
FIG. 13 is real-time screen display of short term trends of various data for another patient having known cardiac disease.

Block 70 describes the running plots of the RAZs ("go/no-go") as well as the voltages for the RMS, HFQE and HFAV of the HF QRS ECG signal versus time for each lead as depicted in FIG. 13. FIG. 13 depicts short-term data in a patient with known CAD wherein the horizontal (time) axis scale is user-adjustable and can be shown either in total or accepted beats (the latter being depicted here) or in seconds. Clinicians can utilize these trends to assess how a monitored patient's cardiac function has changed over time, up to and including the present time. Specifically, clinicians can identify whether and when RAZs have developed or disappeared during the period of monitoring, as well the degree to which the RMS and related voltages of the HF QRS complex have changed over the same period of monitoring. Realization of such changes is particularly valuable to clinicians during situations when the presence or absence of incipient myocardial ischemia or infarction needs to be immediately identified, when the success or failure of invasive or non-invasive treatments administered for ischemia and infarction needs to be immediately recognized, and/or when cardiovascular responses during pharmacological or exercise stress tests or during a patient's ambulatory activities needs to be assessed.

Finally, block 72 describes another feature of the invention, online instantaneous RAZ detection for each lead. The presence of a RAZ within the envelope of the averaged HF QRS signal may be an indication of abnormal cardiac function. As noted above, a RAZ, as originally defined by Abboud (but only in the context of off-line analyses), classically occurs when at least two local maxima of the upper envelope or two local minima of the lower envelope are present within the HF QRS signal. A local maximum or minimum is in turn defined as an envelope sample point (peak or trough) within the QRS interval wherein the absolute value of its voltage exceeds that of the three envelope sample peaks immediately preceding and following it. The RAZ is thus the region lying between the two neighboring maxima or minima. The present invention performs a real-time calculation, looking for local maxima and minima of the QRS envelope not only according to previously published off-line criteria of Abboud (i.e., "$RAZ_A$", or the Abboud RAZ) but also separately and especially according to new criteria that improve the accuracy of 12-lead high frequency QRS ECG for use in cardiac diagnoses in both the offline and online settings.

Figures 16A, 16B:
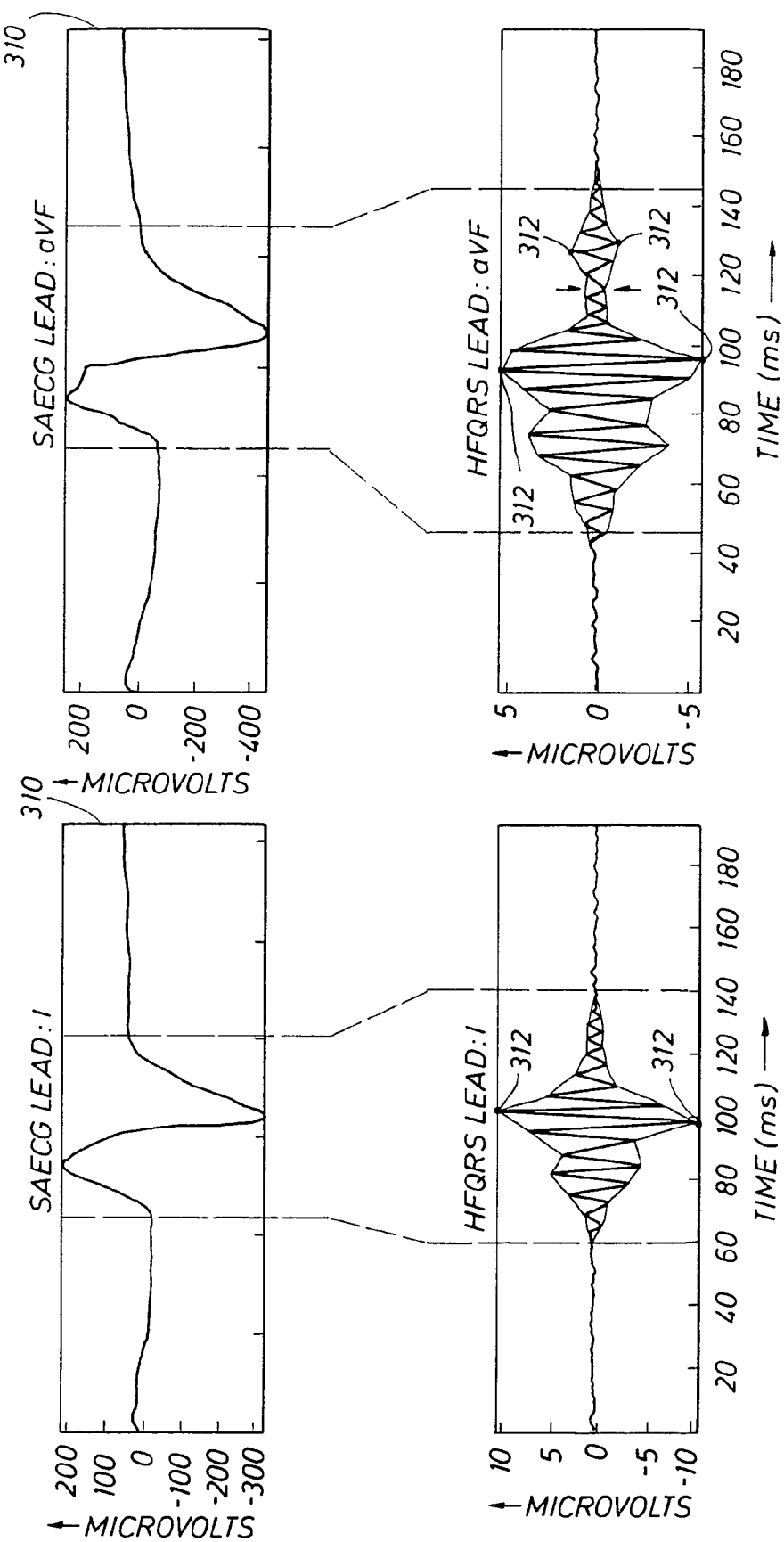
FIGS. 16A, 16B, 16C, and 16D are time plots of cardiac signals to illustrate the Reduced Amplitude Zone variations defined by the present invention.
Figures 16C, 16D:
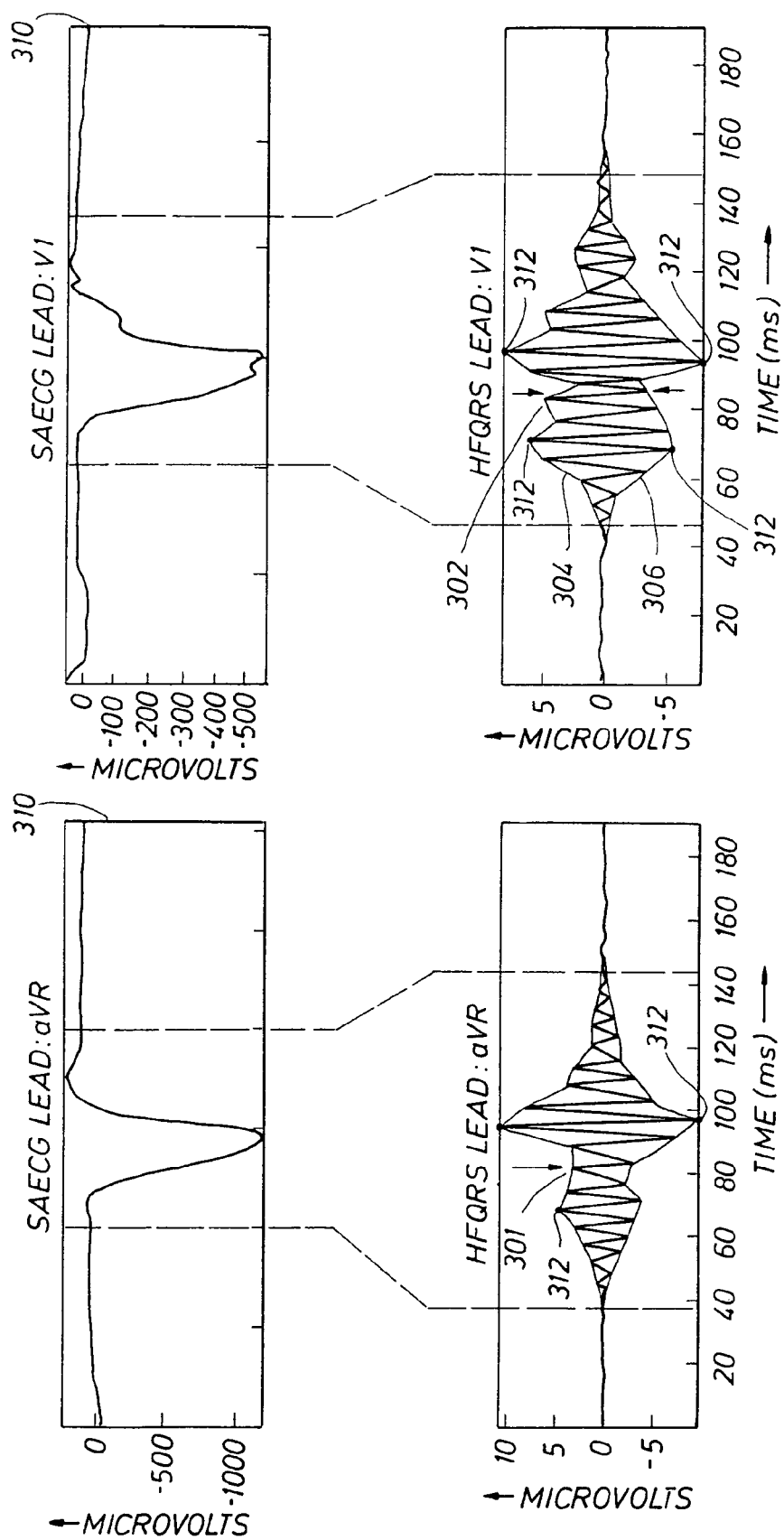
Figure 17:
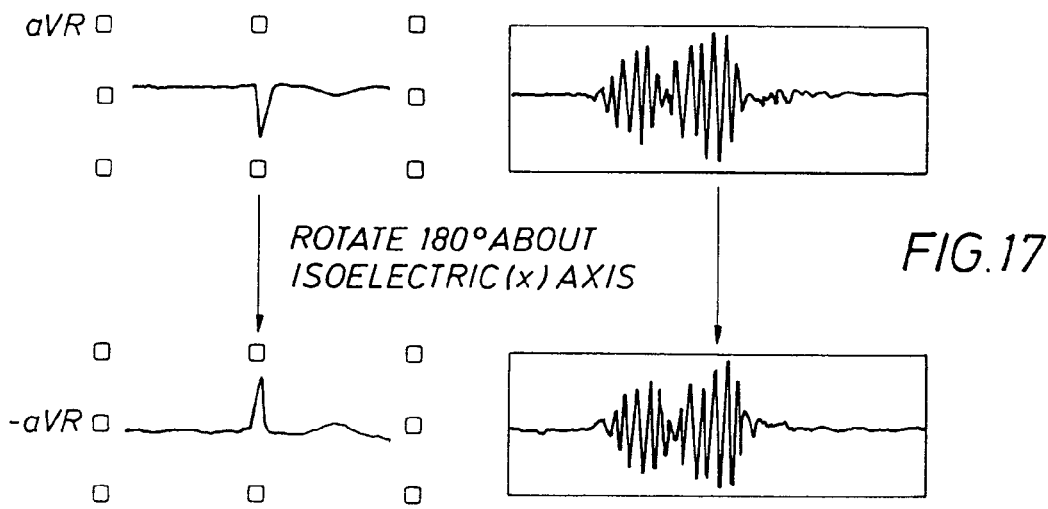
FIG. 17 is a time plot of an ECG illustrating rotation of the image 180° about the isoelectric (x) axis.

One especially important modification contributing to such improvement is the requirement, as shown in FIGS. 16C and 16D, that in order to constitute a stricter type of RAZ, the absolute value of the amplitude of the smaller of the two local maxima (or minima) must be at least a certain percentage of that of the larger of the two local maxima (or minima). When a $RAZ_A$ is present and at least one secondary local maximum (or minimum) also meets this "minimum relative amplitude" requirement, then an "Abboud Percent" RAZ, or $RAZ_{AP}$, is also said to be present (FIG. 16C). When a RAZ is present and at least one secondary local maximum as well as at least one secondary local minimum both meet this "minimum relative amplitude" requirement, then a "NASA RAZ", or $RAZ_N$, is also said to be present (FIG. 16D).

Yet another novel set of user-selectable criteria used in the present invention to assess the presence or absence of a "statistical" type of RAZ concerns the use of real-time calculation of the kurtosis of the incoming HF QRS signal. When present, the kurtosis type of RAZ is referred to as the $RAZ_K$. The presence of a $RAZ_A$, $RAZ_{AP}$, $RAZ_N$, and/or $RAZ_K$ by "go/no-go" indicators on the display, as shown by element 117 in FIG. 7, may also be displayed as a running parameter with time, in a manner similar to FIG. 13.

Figure 8:
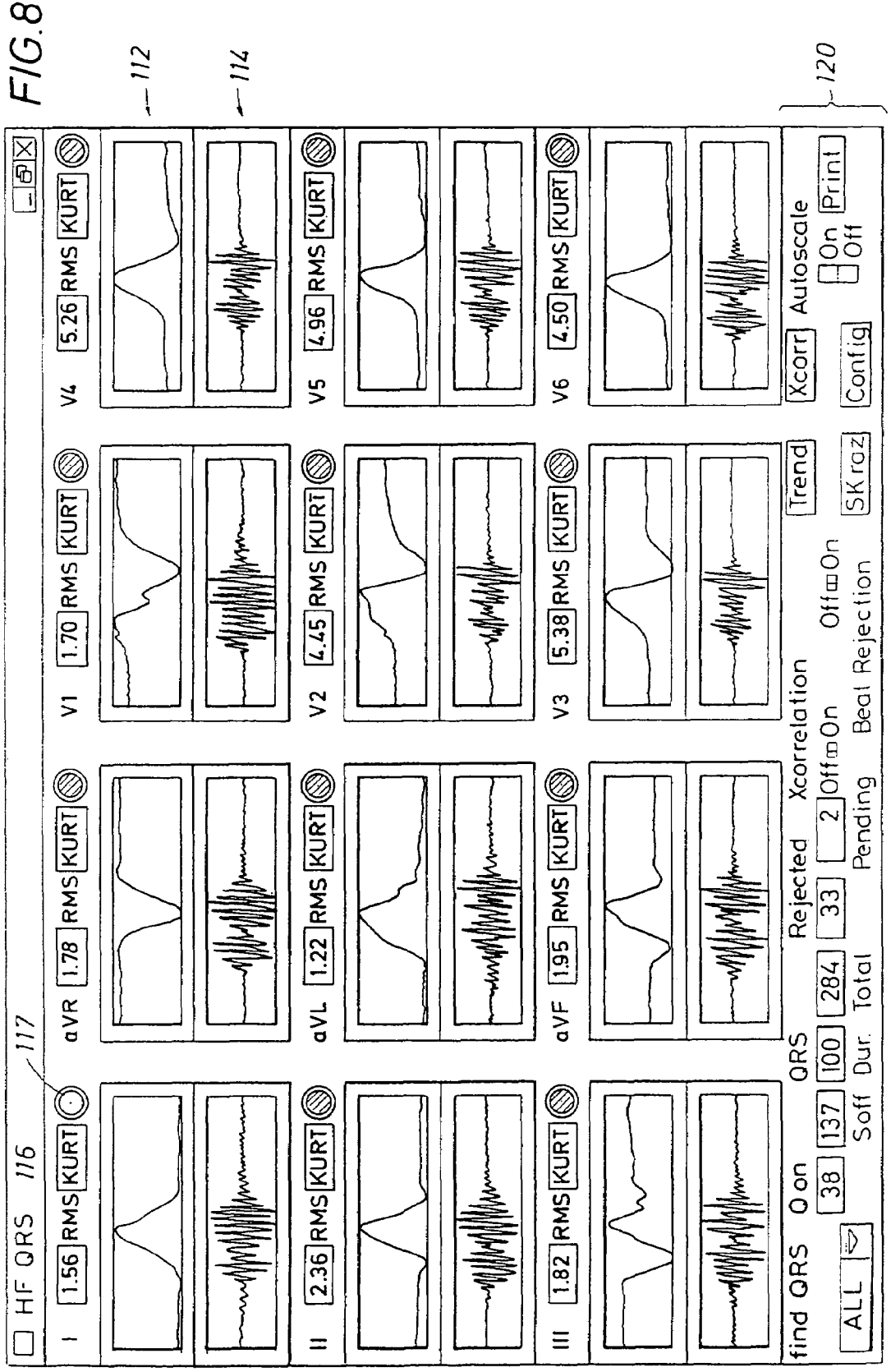
FIG. 8 is a real-time screen display, showing characteristic data obtained from a patient having known cardiac disease, including a side-by-side display of a standard ECG and a filtered ECG.

Referring now more particularly to FIGS. 7 and 8, a feature of the present invention is the simultaneous display in real-time of various aspects of cardiac function with respect to both the conventional and HF QRS ECG. Further, the present invention provides simultaneous, side-by-side or vertical displays of that data to provide the clinician with a tool to compare these aspects of the ECG with one another for a more complete picture of cardiac function than has been previously available. The present invention also displays the conventional and HF QRS 12-lead configurations on one user interface display, while displaying the presence or absence of RAZs on the same display to alert the clinician to potentially abnormal cardiac function.

The display of FIGS. 7 and 8 includes a conventional, signal-averaged ECG signal, designated by the element number 112. The display signal 112 includes the signals from leads I, II, III, aVR, aVL, aVF, displayable in either the conventional or sequential (i.e., aVL, I, –aVR, II, aVF, III) configuration, and the signals from either precordial leads V1-V6 or precordial leads CR1-CR6. The user is given the option of displaying the limb leads in the sequential configuration in order to facilitate judgments regarding lead contiguity. The user is given the option of using the CR leads, wherein the reference for the precordial signals is the right arm electrode rather than Wilson's central terminal, because the CR lead configuration results in larger absolute QRS voltages than the V precordial lead configuration, potentially enhancing HF QRS diagnostic sensitivity. Further, the display of the conventional signal average 112 is updated with each beat, as a reference for the clinician. Positioned immediately adjacent to or below the conventional ECG display 112 is a display 114 of a running, instantaneous filtered (i.e. HF) QRS ECG signal, one for each of the twelve leads, corresponding to the individual leads of the display 112. The display signal 114 includes the signals from leads I, II, III, aVR (or –aVR), aVL, aVF, and V1-V6 (or CR1-CR6) to correspond to like signals in the display 112. Above each HF QRS signal are the instantaneous RMS and kurtosis values 116 and 116', respectively, in that particular lead, and an instantaneous RAZ indicator 117, color-coded to indicate the RAZ type(s) that are actually present.

At the bottom of the screen display of FIGS. 7 and 8 is a tool bar 120. The tool bar 120 provides user control and display of various data useful to the clinician. The tool bar includes a user selectable indicator 122 in which the user can select which of a plurality of QRS complexes will be used to define the unfiltered QRS interval(s). Displays 124, 126, and 128 show the timing of the QRS onset, QRS offset, and the duration of the QRS complex, respectively. A display 130 shows the total number of heartbeats which have been detected during any particular recording, while a display 132 shows the number of beats rejected and a display 134 shows the number of beats whose processing is pending, if any. Toggle buttons 136 and 138 permit the user to turn on and turn off the cross correlation function and the beat rejection function, respectively. Display buttons 140, 142, 144, and 146 permit the user to select other displays for the screen, as shown. A toggle button 148 permits the user to turn on and turn off an autoscale function, and a print button 148 permits the user to print a particular screen capture at his discretion.

Of particular note, in comparing FIGS. 7 and 8, is the small number of RAZs and lit RAZ indicators 117 for the healthy patient shown in FIG. 7, versus the much larger number of RAZs and lit RAZ indicators for the subject with known CAD, shown in FIG. 8.

Figure 9:
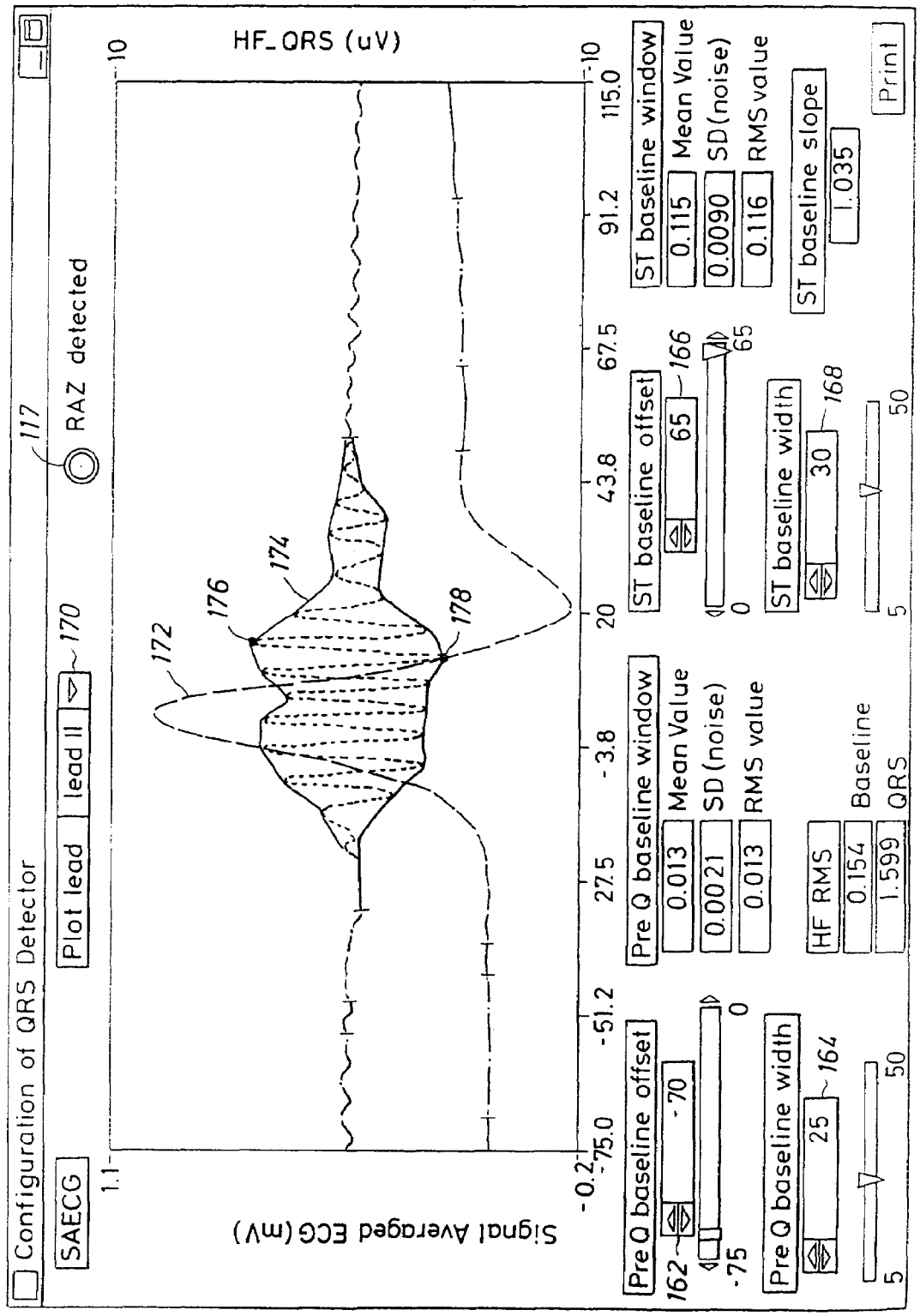
FIGS. 9 and 10 are real-time screen displays, showing the configuration of a QRS detector for a normal, healthy subject and for a patient having known cardiac disease, respectively.
Figure 10:
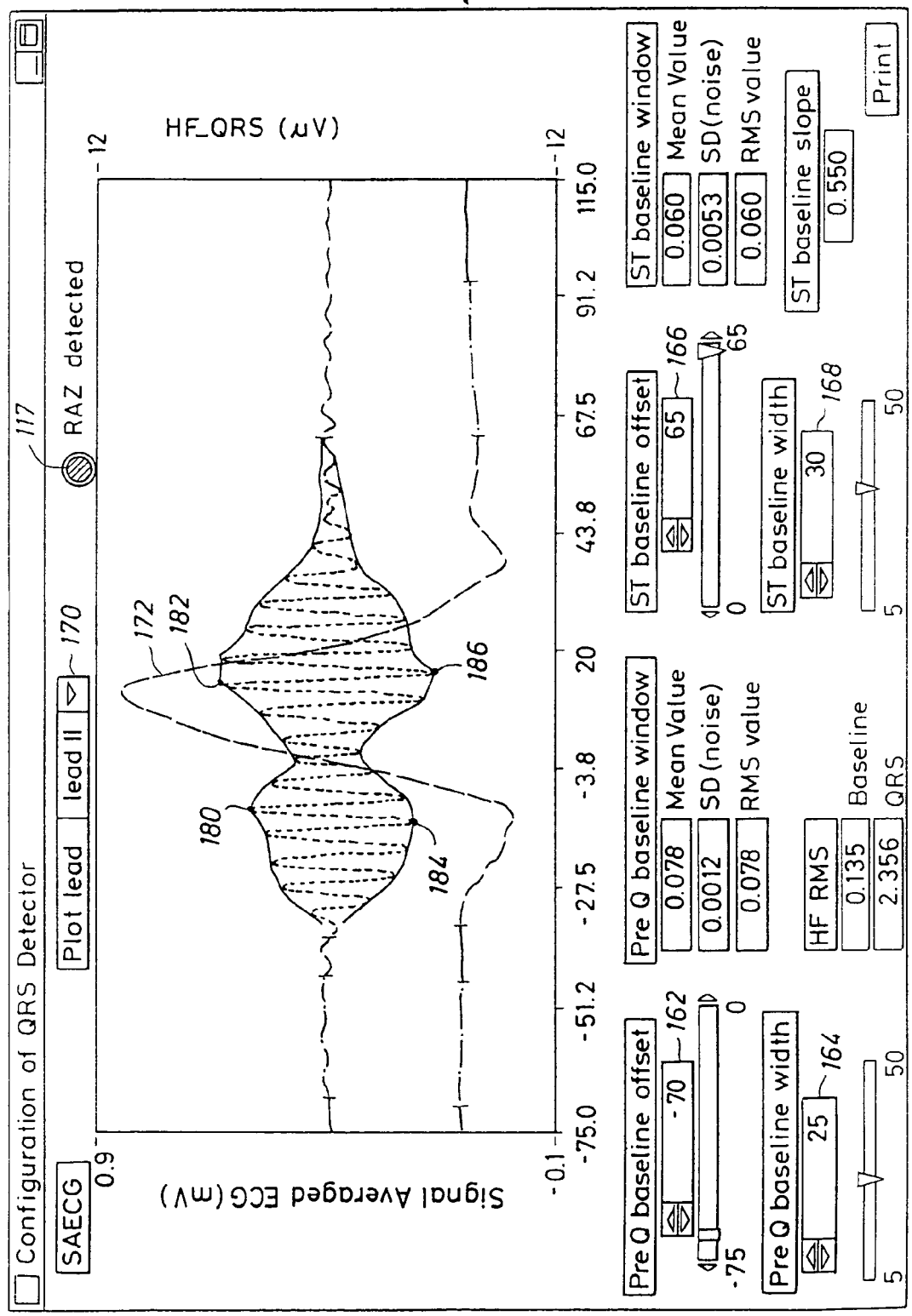

FIGS. 9 and 10 show configuration screen 160 for the online QRS interval detector of the invention, selectable by button 146 of FIGS. 7 and 8. The configuration screen of FIGS. 9 and 10 permits the user to select a period within the P-R interval of the ECG, with specific pre-Q offset and interval width selectors 162 and 164, respectively, that will aid in the determination of the onset of the QRS complex. The values for these parameters shown in FIGS. 9 and 10 have been selected based on initial experience to provide satisfactory performance of the invention for the broadest array of subjects, since cardiac function typically varies from patient to patient. Similarly, selectors 166 and 168 permit the user to select the offset and width, respectively, of a portion of the ST segment that will aid in the determination of the offset of the QRS complex. The configuration screen 160 also displays various parameters measured from the current heartbeat, as shown. An indicator 170 shows the user which of the leads is selected, in the case of FIGS. 9 and 10 that lead is lead II. A RAZ indicator 117 is also provided for the convenience of the user.

FIGS. 9 and 10 also include superimposed displays of a conventional QRS signal average 172 and its associated averaged filtered (HF) QRS signal 174. The ordinate on the left of FIGS. 9 and 10 shows the averaged conventional signal 172 in millivolts, and the ordinate on the right shows the averaged HF signal 174 in microvolts.

FIG. 9 shows a single local maximum 176 and a single local minimum 178. However, FIG. 10, depicting the waveforms for a patient with known CAD, shows two local maxima 180 and 182, and two local minima 184 and 186. Since the maxima and/or minima occur within the QRS complex, and are separated by at least three envelope sample points with lesser absolute amplitudes between them, they define a reduced amplitude zone as also shown on the lit RAZ indicator 117.

FIGS. 11 and 12 depict cross correlation screens 190 of the invention. This display may be referred to as the cross correlation panel. The screen 190 is selected by a user with button 144 (FIG. 7). The screen includes a display 192 of a conventional QRS signal average (i.e., any one of the multiple QRS templates being derived), averaged over a user selectable number of beats. A display 194 shows the conventional QRS complex of the current incoming beat, and a display 196 shows the cross correlation between the waveforms of display 192 and display 194. A user may select the threshold for the cross correlation, below which the beat is rejected, by a selector 197 and, if a beat is rejected, an indicator light 198 illuminates. A digital display 191 on the right side of the cross correlation panel shows both the instantaneous and the summarized cross-correlations for all channels simultaneously. This digital display also updates from one beat to the next. Moreover, the user can use this digital display to troubleshoot observed excessive rejections of beats. In other words, the display 191 allows the user to determine which leads or channels contain the most rejected beats, and in turn to physically adjust those leads most affected by rejected beats in order to proceed with an overall less noisy recording. The display 191 further provides instantaneous cross-correlation and R-wave jitter correction of the new beat versus the template beat in each individual channel, and a mean cross-correlation of all beats in a channel so far versus the templates that have existed for that channel, as shown in FIG. 11.

Note that the display 191 provides a visual display of the instantaneous and past cross-correlations within all eight channels simultaneously, another feature of the present invention. Further, the display 196 depicts the cross-correlation function and jitter correction of all eight channels on a single display, preferably with each function in a different color. The panel 190 also includes a user-selectable threshold 195 permitting the user to select rejection based on how many channels fail correlation, shown in FIG. 11 as set to "1", such that any beat rejected in any channel gets rejected in all channels.

Note also that in FIG. 12 the current heartbeat shown on the display 194 is noisy and has a different shape than the template. The current beat is also shifted in time from the template of display 192. Consequently, the cross correlation between them is poor, as reflected in the display 196, which only has a peak of 0.958 (i.e. below the user selectable threshold set at 0.970 in this case) and the beat is rejected, as shown by the indicator light 198. Thus, the current beat is not incorporated into the running templates of the averaged ECG.

By comparing the displays in FIGS. 11 and 12, one can see that the patient whose cross-correlation is shown in FIG. 11 has had roughly 30% of the beats rejected, mostly because of poor cross-correlation in channel I. One the other hand, in FIG. 12, 81.8% of the beats have been rejected due to poor cross-correlations in several different channels, suggesting an overall poor preparation of the electrodes or some other more global source of noise.

FIG. 13 depicts trend lines for the RMS, HFQE, HFAV and kurtosis, and shows the current value for these parameters, for a patient with known heart disease. This display further includes lines depicting the presence versus the absence of the $RAZ_A$, $RAZ_{AP}$ and $RAZ_N$ as described herein. This display illustrates another feature of the present invention, that of showing a trend of parameters over time. Specifically, the trend lines shown on a screen 200, which are continuously updated in real time, illustrate the presence (versus the absence) of all defined types of RAZs over a user-selectable period of time (always up to and including the present time) as well as the trends for RMS, HFQE, HFAV and kurtosis over this same user-selectable period of time for all the leads attached to the patient. A similar but longer-term trend line plot can also be generated (for example with thousands of beats rather than hundreds of beats on the x axis), and the short and long-term trend line plots can be accessed simultaneously by the user. To reiterate, the time intervals (horizontal axes depicted here in units of beats) on any of these plots are completely selectable by the user. The particular parameters depicted on the plot shown are intended to be illustrative only, and other parameters may be similarly illustrated. The ordinate for each plot is in microvolts with respect to the RMS, HFQE and HFAV and is unitless for kurtosis. (The RAZs are also unitless, being "go versus no-go" entities). The abscissa can be in either beats or seconds, for characterization of the trend.

Figure 14B:
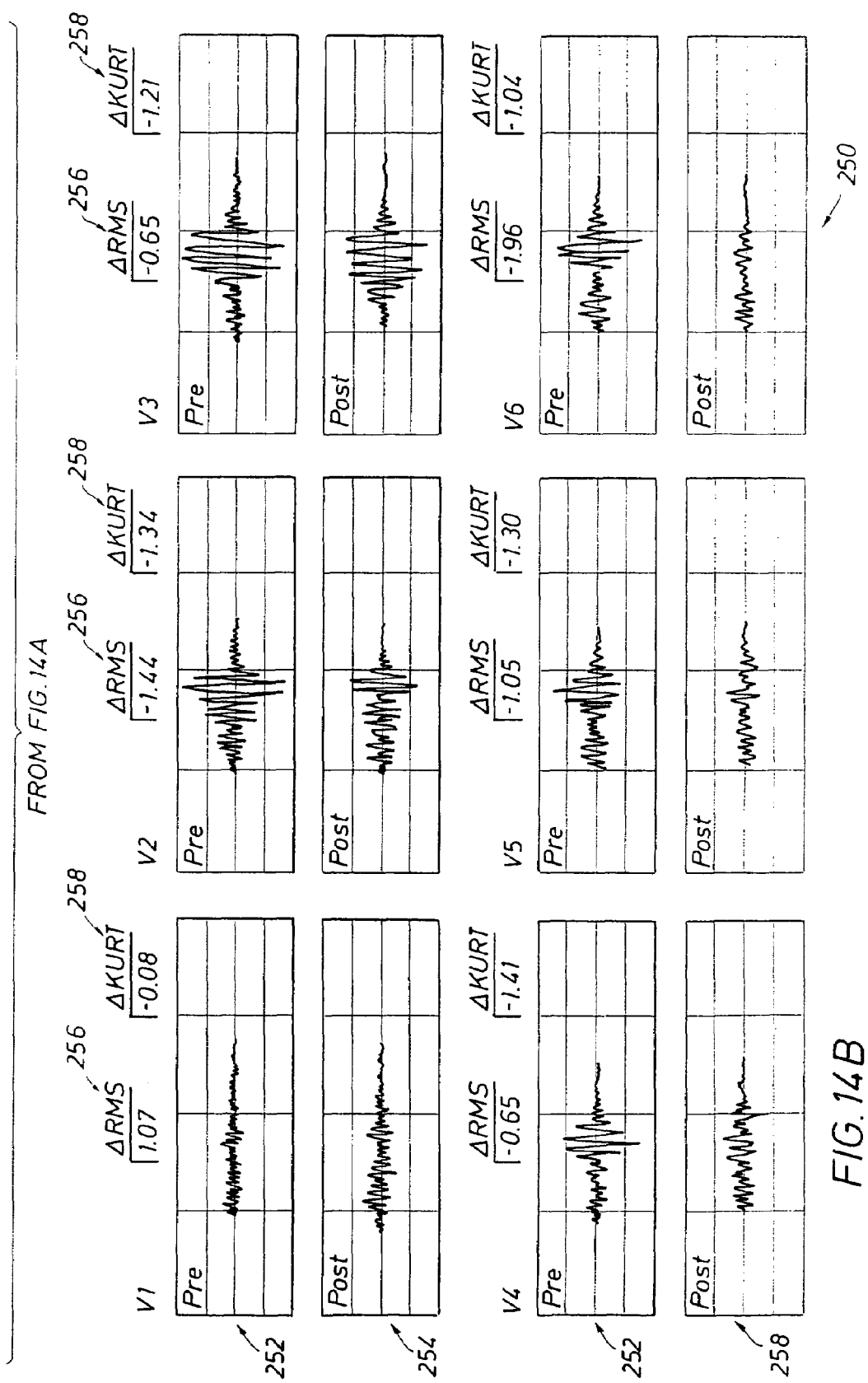
FIG. 14 is a real-time screen display of a "baseline" 12-lead frequency QRS recording (PRE measurements), collected at some time previously, compared to the present 12-lead high frequency QRS recording (POST measurements), in a patient who suffered an MI between the two time periods.

FIG. 14 illustrates another feature of the present invention. FIG. 14 depicts a display 250 which plots a baseline 12-lead HF QRS recording 252, such as for example, a pre-angioplasty recording, juxtaposed with a current, dynamic QRS display 254. The display 250 further includes a ΔRMS reading 256 and a ΔKurt (Δkurtosis) reading 258, to dynamically display the differences between the baseline, or "pre-procedure" readings, and current, or "post-procedure" readings for comparison. This feature can also provide an indicator of gain or loss of any type of RAZ between the two time points. The tracings shown for illustration purposes are for a patient who suffered an angioplasty-induced MI between the baseline 252 and current 254 time points.

Numerical measures of the HF QRS ECG may be calculated in several ways. These measures are important because they often decrease when ischemia is present. Perhaps the most popular measure is the root mean square (RMS) voltage of the QRS signal, which is equivalent to the "area under the curve" of the power spectrum, defined as $$RMS = \sqrt{\frac{\sum_{i=ufqon}^{ufqoff} X_i^2}{UFQRSD}}$$

where $X_i$ is the filtered voltage at a given sampling point, ufqon and ufqoff are the onset and offset, respectively, of the QRS interval, and UFQRSD is the unfiltered QRS interval duration as defined by ufqon and ufqoff. In this context, the term "onset" means the start of the QRS interval, and the term "offset" means the end of the QRS interval. This is the primary numerical measure used in preferred embodiment of the present invention.

Other numerical measures of the HF QRS signal have also been proposed (and used strictly in an off-line fashion) by Xue et al. (see Xue, Q., B. R. Reddy, and T. Aversano. Analysis of high-frequency signal-averaged ECG measurements. *J Electrocardiol* 28: 239-45, 1995). These numerical measures include the high frequency integral of absolute values (HFAV) and the high frequency QRS energy (HFQE). Xue et al. have defined HFAV and HFQE as follows:

$$HFAV = \sum_{i=uqon-10ms}^{uqoff+10ms} |X_i - AVNL|$$

and, $$HFQE = \sum_{i=uqon-10ms}^{uqoff+10ms} (X_i - AVNL)^2$$

wherein AVNL equals the average noise level of the filtered signal in the ST segment in a 40 ms window located 60 ms from the QRS offset. It should be noted that in their own definitions for HFAV and HFQE (as shown above), Xue et al. "pad" both the QRS onset and offset by extra 10 ms each in an effort to reduce noise and noise variability, presumably to compensate for potential inaccuracies and inconsistencies related to the determination of the QRS interval.

In the presently preferred embodiment of the invention, the definitions for HFAV and HFQE are modified in two ways. First, because the present invention provides a means of viewing the high and low frequency ECG signal in real time, thereby providing reliability for the determination of the QRS interval, the necessity (or lack thereof) of using the 10 (or alternative) millisecond padding periods is left to the discretion of the user. Second, the present invention preferably uses the PR interval or TP segment rather than the ST segment to determine the AVNL of the baseline, since a segment of the cardiac cycle wherein neither myocardial cell depolarization nor repolarization is occurring is preferred. In the device of the present invention disclosed herein, AVNL is determined as the RMS noise of the filtered signal that is within a 25 ms interval in the PR segment.

In a preferred embodiment, HFAV is measured as:

$$HFAV = \frac{\sum_{i=uqon}^{uqoff} \||X_i| - AVNL\|}{UFQRSD}$$

wherein AVNL (average noise level) equals the "noise" of the high frequency (i.e., filtered) signal within that portion of the PR interval just noted and UFQRSD is unfiltered QRS duration.

Further, high frequency QRS energy (HFQE) is calculated as:

$$HFQE = \frac{\sum_{i=uqon}^{uqoff} (|X_i| - AVNL)^2}{UFQRSD}$$

wherein AVNL is determined in the same way as for HFAV.

A useful characterization of a set of data includes skewness and kurtosis. Skewness is a measure of symmetry, or more accurately, the lack of symmetry. A distribution, or data set, is symmetric if it looks the same to the left and right of the center point. Kurtosis is a measure of whether the data are peaked or flat relative to a normal distribution. That is, data sets with a high kurtosis tend to have a distinct peak near the mean, decline rather rapidly, and have heavy tails. Data sets with low kurtosis tend to have a flat top near the mean rather than a sharp peak. A uniform distribution would be the extreme case. By determining the skewness and kurtosis of individual HF QRS signals, and by displaying the skewness values alone, the kurtosis values alone, or skewness versus kurtosis graphically with one value on the ordinate and the other on the abscissa, the clinician may obtain information from the HF QRS signals potentially indicative of cardiac disease. This is described in further detail below with respect to the currently preferred embodiment.

Currently Preferred Embodiment

Figure 15:
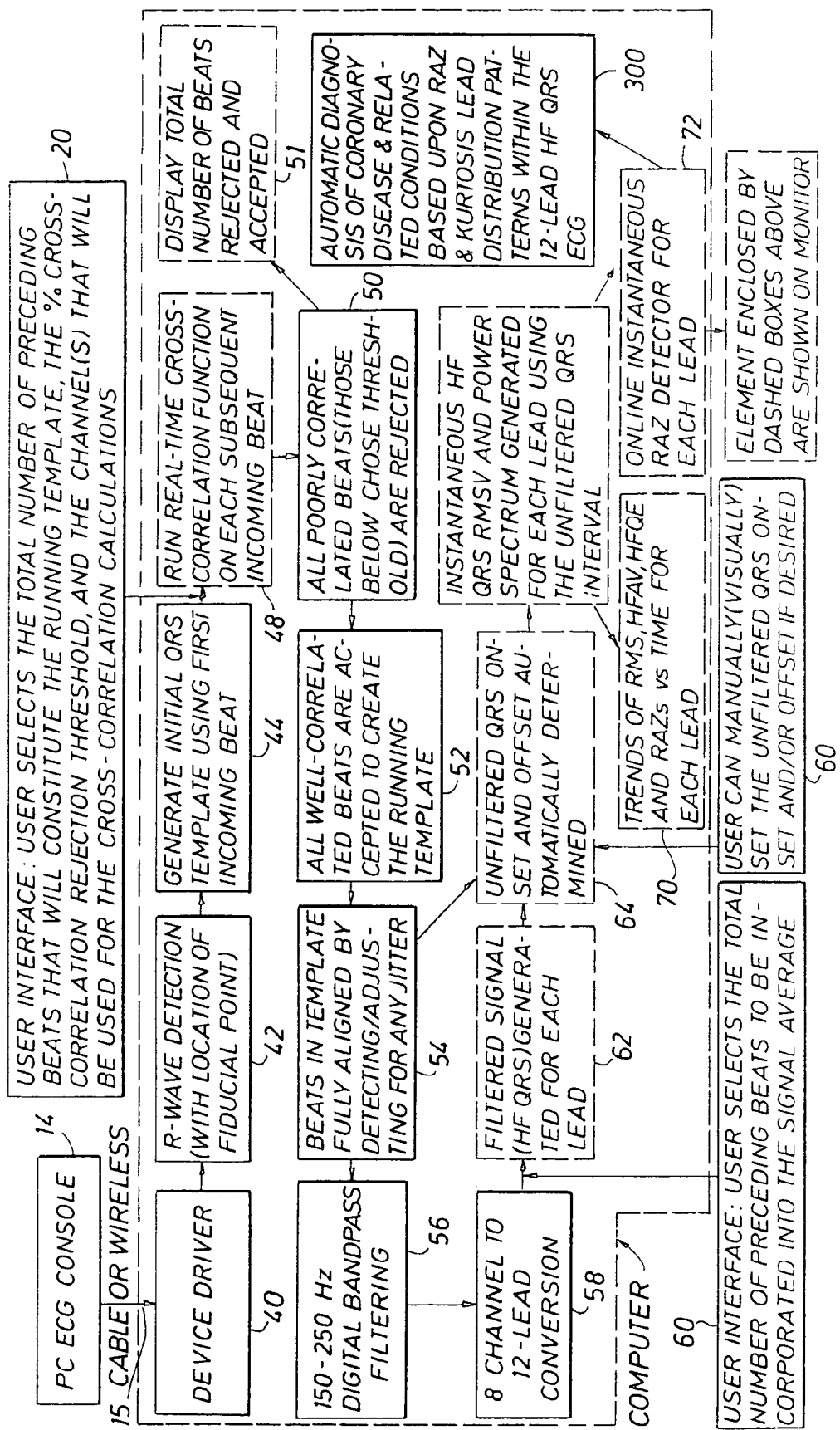
FIG. 15 is a schematic diagram of the logic carried out by the system with the addition of the present invention.

As previously described, additional sets of RAZ criteria improve the overall sensitivity and specificity of detecting CAD, myocardial ischemia and infarction and other heart conditions using 12-lead HF QRS electrocardiography. The logic illustrated in FIG. 15 is the same as that previously described in respect of FIG. 6, with the exception of an additional automatic diagnosis component 300, and the previous description FIG. 6 is incorporated here as if repeated, but is omitted here for brevity. The automatic diagnosis component 300 receives signals regarding RAZs from the instantaneous RAZ detector 72, as previously described.

To describe the analysis performed by the component 300, a series of ECG signals are depicted in FIGS. 16A through 16D. FIG. 16A illustrates an example of a "normal" HF QRS complex, in which no RAZ has been detected. FIGS. 16B through 16D illustrate "abnormal" HF QRS complexes in which RAZ types of ascending severity have been detected through use of additional criteria analyzed by the component 300. The envelope of the HF QRS signal in FIG. 16B has both a primary local maximum and a secondary local maximum. A $RAZ_A$ is therefore present. (The same envelope also has a primary local minimum and a secondary local minimum, which too are sufficient to form a $RAZ_A$). However, the requirement that the voltage of any secondary local maximum on the envelope be at least X% of that of the primary local maximum, or that the voltage of any secondary local minimum on the envelope be at least X% of that of the primary local minimum, has not been met by the signal in FIG. 16B. In the system software as presently preferred, X% tentatively defaults to 30%, based empirically upon data collected from individuals with and without CAD, but the percentage is user-adjustable and can be changed at any time to suit the specific diagnostic need or population being studied. When a $RAZ_A$ is present and its secondary local maximum (or minimum) meets this "X% (e.g., 30%) or more of the primary local maximum (or minimum)" additional requirement, then an "Abboud Percent" RAZ ($RAZ_{AP}$) is also said to be present. This defined $RAZ_{AP}$ is illustrated in FIG. 16C as RAZ 301. Furthermore, when two local maxima of an upper envelope 304 and (rather than or) two local minima of a lower envelope 306 are present within the HF QRS signal, and when both the secondary local maximum and the secondary local minimum meet the "X% (e.g., 30%) or more of the primary local maximum (minimum)" additional requirement, then a very strict type of RAZ known as the "NASA RAZ" ("$RAZ_N$") is also said to be present, shown as RAZ 302 in FIG. 16D.

FIGS. 16A through 16D are screen snapshots showing HF QRS complexes below their respective signal-averaged conventional QRS complexes 310. The darkened circular points 312 in the HF QRS signals connote envelope local maxima and minima, whereas arrows, when present (FIGS. 16B through 16D), connote a RAZ.

In FIG. 16A, an HF QRS complex from lead I is shown that contains no RAZs. This complex is "normal". In FIG. 16B, an HF QRS complex from lead aVF contains an "Abboud RAZ" ($RAZ_A$) on both the right upper and lower portions or envelopes of the signal. The amplitudes of both the secondary local maximum and minimum are nonetheless insufficient to define an "Abboud Percent" RAZ ($RAZ_{AP}$), because they are less than 30% (empirically defined) of the amplitudes of their corresponding primary local maximum and minimum. In FIG. 16C, an HF QRS complex from lead aVR has a $RAZ_{AP}$ 301. The $RAZ_{AP}$ is present because the absolute amplitude of the secondary local maximum (left side of signal) that forms the RAZ is $\geq 30\%$ of that of the corresponding primary local minimum.

Finally, in FIG. 16D, an HF QRS signal has a "NASA RAZ" ($RAZ_N$) 302. A $RAZ_N$ is present because both a secondary local maximum and a secondary local minimum are present and both have amplitudes exceeding 30% of the amplitudes of their respective primary local maximum/minimum. Note that whenever a $RAZ_N$ is present in any given HF QRS complex, a $RAZ_{AP}$ and $RAZ_A$ must also be present by definition, and similarly whenever a $RAZ_{AP}$ is present, a $RAZ_A$ must also be present by definition.

As already noted, another novel set of criteria used in the innovation to assess the presence or absence of a "statistical" type of RAZ concerns the calculation of the kurtosis of the incoming HF QRS signal. In the presently preferred embodiment, to determine the kurtosis of an HF QRS signal in real time, the absolute value in microvolts of the envelope sample points is plotted against time in milliseconds. The resulting figure, when normalized to have an area of 1.0, can be thought of as a probability density function with central moments $\mu_k = \int (t-\mu)^k f(t) dt$ (k=1, 2, ...), where f(t) is the normalized absolute voltage at sample point t and $\mu = \int t f(t) dt$. The kurtosis ($\gamma$) is the normalized fourth moment $$\gamma = \frac{\mu_4}{\mu_2^2}.$$

Because a bimodal distribution has a relatively low kurtosis, and because the presence of a RAZ may cause the shape of an HF QRS envelope to resemble a bimodal distribution, HF QRS signals with RAZs typically have a low kurtosis. By applying the statistical concept of kurtosis to an HF QRS signal itself, mathematically more robust information concerning the shape of the HF QRS signal may be obtained than from other measures such as the $RAZ_A$. At the present time, the software automatically separates the kurtosis characteristic of each HF QRS signal into "normal" and "low" categories. An individual HF QRS ECG signal having a kurtosis value of greater than 2.65 is presently designated as "normal" with respect to kurtosis—i.e., it has no "kurtosis RAZ" ($RAZ_K$) present within it. On the other hand, a HF QRS signal with a kurtosis value of less than 2.65 is presently designated as "abnormal", and is considered to have a $RAZ_K$ present within it. The presence of a $RAZ_K$ is important because, as will be explained in greater detail below, the $RAZ_K$ and the $RAZ_{AP}$ are often considered interchangeable from a diagnostic standpoint. The cut-off value noted here for kurtosis is given strictly to provide an illustration of the spirit of the use of kurtosis in present innovation. Similar to the $RAZ_{AP}$ percentage cut-off values, the exact kurtosis cut-off values ultimately utilized for clinical purposes are subject to change based upon several factors, including but not limited to the specific cardiac condition that one is attempting to diagnose; the exact number of beats that are in the signal average; the specific channel or channels being used to provide the HF QRS ECG cross correlation template(s) for beat rejection; and the specific version of the ECG hardware or analysis software being used (i.e., type of R-wave detector being utilized, degree of jitter present in the R-detector, etc.).

When the presence or absence of a $RAZ_N$, $RAZ_{AP}$, $RAZ_A$ and/or $RAZ_K$ is evaluated in the system of FIG. 15, a "pad" of 10 ms is also preferably included on both sides of the QRS interval, because such padding reduces noise and noise variability while also compensating for any potential inaccuracies and/or inconsistency related to the determination of the QRS interval duration. In the present invention, the skewness (a statistical determination of a lack of symmetry) of the individual HF QRS signals is also measured.

As previously described, it is known in the art, using off-line analysis, to employ only three of the standard 12 ECG lead positions and to define a positive test for CAD as one in which a $RAZ_A$ is present in at least two of these three selected precordial leads. The present invention, however, uses a set of 12-lead HF QRS ECG criteria, thereby providing an ability to more sensitively and specifically identify the presence/absence of CAD and other heart conditions. The 12-lead criteria will now be described in detail.

All included criteria listed below are based on multi-beat signal averaged ECG recordings that have acceptable signal-to-noise ratios (generally requires $\geq 50$ beats) and that use the results of cross-correlation in any one or more of the ECG channels as the criterion for individual beat acceptance versus rejection. A given RAZ can be considered present either when it occurs during at least X% (preferably 50%) of all (or some portion of) the accepted beats constituting the recording (preferably the entire recording, but a user-adjustable portion may be used). Alternatively, a RAZ can be considered present when it occurs at only at the very end of the recording, when the signal-to-noise ratio is at its greatest.

In one aspect, the present invention defines a set of criteria indicative of CAD or an ACS, as determined by the apparatus described above. When complicating cardiac conditions such as bundle branch blocks, heart failure, ventricular hypertrophy, extreme axis deviation, paced rhythms and arrhythmias are not present, then a multi-beat 12-lead HF QRS ECG recording with a sufficient signal-to-noise ratio is suspicious for CAD or an ACS when:

1) A $RAZ_N$ is present in each of three or more spatially contiguous HF QRS ECG leads; or, 2) A $RAZ_{AP}$ and/or $RAZ_K$ is present in each of four or more spatially contiguous HF QRS ECG leads, or 3) A $RAZ_{AP}$ and/or $RAZ_K$ is present in each of five or more total HF QRS ECG leads when the five or more affected leads are distributed as follows: Either in: a) two or more spatially contiguous limb leads plus in three or more spatially contiguous precordial (i.e., V or CR) leads, and/or in b) three or more spatially contiguous limb leads plus in two or more spatially contiguous precordial (i.e., V or CR) leads.

Cases 2) and 3) are specific cases wherein $RAZ_K$ and $RAZ_{AP}$ are considered diagnostically interchangeable. That is, the $RAZ_{AP}$ and $RAZ_K$ can substitute for one another in any mixed combination toward fulfilling either of these case's criteria.

"Spatial contiguity" is defined somewhat differently when identifying RAZs in the context of 12-lead HF QRS electrocardiography than when identifying potential ischemic changes in the context of 12-lead resting or exercise stress test conventional electrocardiography. The reason for this difference is demonstrated in FIGS. 17 and 18.

Figure 18:
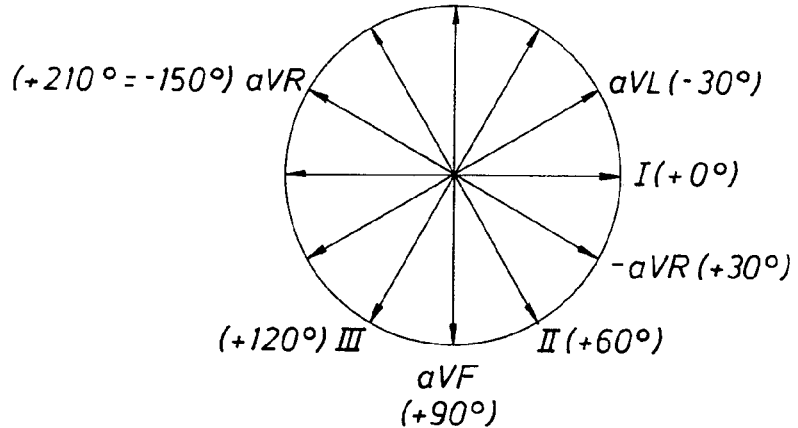
FIG. 18 is a diagram illustrating the practical equivalence of HF QRS signals from the standpoint of RAZ detection when rotating the image as shown in FIG. 17.

When conventional lead aVR is flipped 180° about its x (isoelectric) axis (upper left side of FIG. 17), it becomes conventional lead-aVR, and the frontal plane vector it reflects changes from +210° (aVR) to +30° (−aVR) (as shown in FIG. 18). However, when the HF QRS tracing from the same lead is flipped in the same fashion (upper right side of FIG. 17), even though the frontal plane vector changes similarly, any RAZ that is present (or absent) prior to the flipping will always remain present (or absent) after the flipping. Thus, strictly from the standpoint of detecting RAZs in HF QRS tracings, lead aVR is equivalent to lead −aVR. Furthermore, this same concept of practical equivalence with respect to RAZ detection also applies to all of the other limb leads and their respective counterparts located 180° away in the frontal plane.

Because HF QRS lead aVR is, from the perspective of RAZ detection, therefore located both at +30° degrees and at +210° in the frontal plane, it is therefore spatially contiguous to (i.e., only 30 degrees away from) the signals located both in lead I (+0° in the frontal plane axis) and lead II (+60° in the frontal plane axis).

Figure 19A:
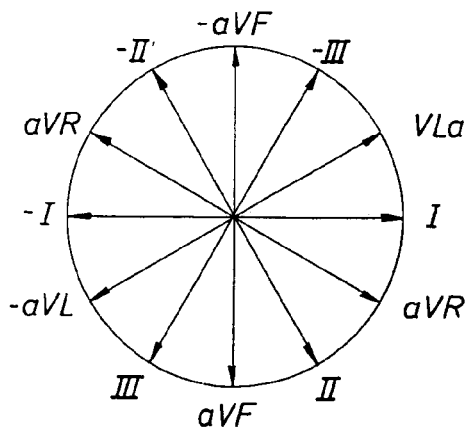
FIGS. 19A and 19B are diagrams illustrating what is meant by contiguous lead zones in the present invention.
Figure 19B:
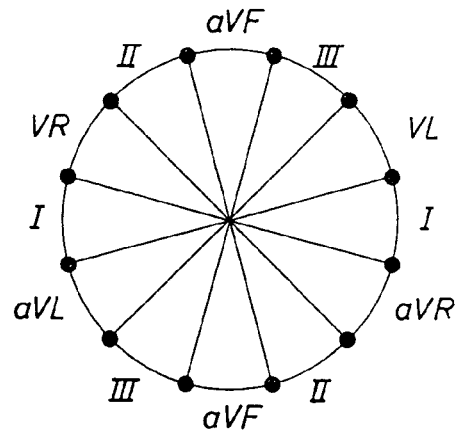

Furthermore, as can be construed from FIGS. 19A and 19B, there are therefore six sets of "three contiguous leads" that can be derived from the six frontal plane leads for use in RAZ detection in 12-lead HF QRS electrocardiography. These are:

set 1=leads III, aVL and I;
set 2=leads aVL, I and aVR;
set 3=leads I, aVR and II;
set 4=leads aVR, II and aVF;
set 5=leads II, aVF and III; and
set 6=leads aVF, III and aVL.

Referring again to FIGS. 19A and 19B, there are also six sets of "four contiguous leads" that can be derived from the six frontal plane leads:

set 1=leads III, aVL, I and aVR;
set 2=leads aVL, I, aVR and II;
set 3=leads I, aVR, II and aVF;
set 4=leads aVR, II, aVF and III;
set 5=leads II, aVF, III and aVL; and
set 6=aVF, III, aVL and I as well as six sets of "five contiguous leads" that can be derived from the six frontal plane leads in a similar fashion:

set 1=all frontal plane leads except lead III;
set 2=all frontal plane leads except lead aVL;
set 3=all frontal plane leads except lead I; and so forth.

Figure 20:
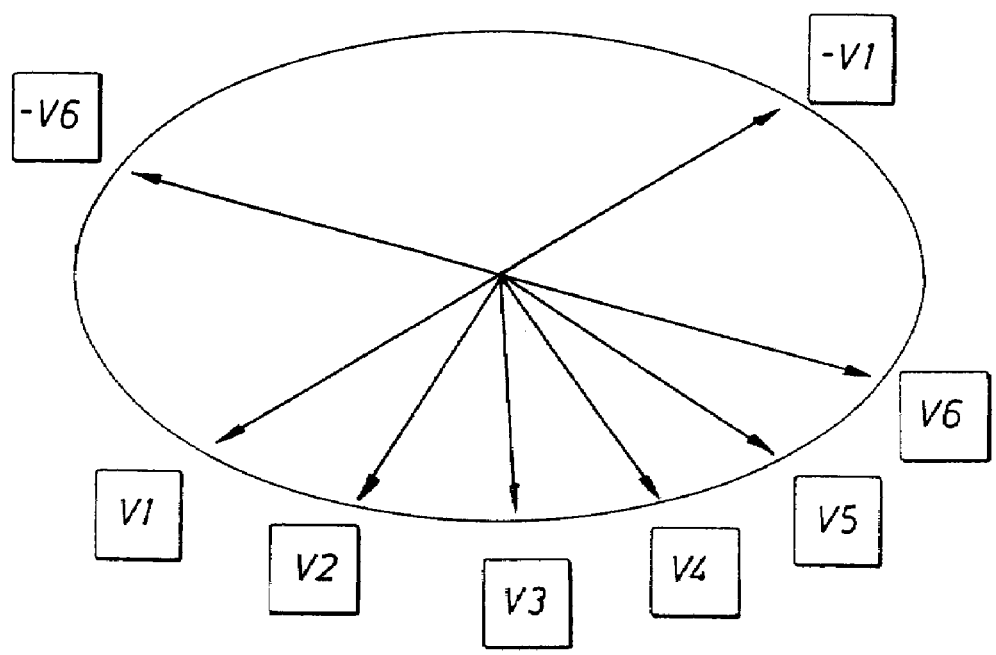
FIG. 20 is a diagram illustrating the non-equivalence of certain precordial and theoretical leads in the present invention.

Moreover, as can be seen from FIG. 20, there are also four sets of "three contiguous precordial leads" for each type of precordial lead configuration:

set 1=leads V1-V3 (or CR1-CR3);
set 2=leads V2-V4 (or CR2-CR4);
set 3=leads V3-V5 (or CR3-CR5); and
set 4=leads V4-V6 (or CR4-CR6), as well as three sets of "four contiguous precordial leads" for each configuration:

set 1=leads V1-V4 (or CR1-CR4);
set 2=leads V2-V5 (or CR2-CR5); and
set 3=leads V3-V6 (or CR3-CR6).

Two sets of "five contiguous precordial leads" are also provided that can be derived from either precordial lead configuration for 12-lead HF QRS electrocardiography: leads V1-V5 and leads V2-V6 (or leads CR1-CR5 and leads CR2-CR6).

As shown in FIGS. 19A and 19B, when the six frontal plane leads are plotted together with their respective counterparts that are 180° away in frontal plane, the 12 resultant leads form a circle with increments at every 30° in the frontal plane (FIG. 19A). The resulting lead "zones" that can be derived from this (FIG. 19B) are used in the present invention in the following specific fashion: When $RAZ_N$s are present in at least three contiguous HF limb lead zones as shown in FIG. 19B (for example, in HF QRS leads III, aVL, and I simultaneously, or in HF QRS leads aVL, III and aVF simultaneously, as described above), or when $RAZ_{AP}$s and/or $RAZ_K$s are present in at least four contiguous HF limb lead zones as shown in FIG. 19B (as described above in respect of the six possible combinations of "four contiguous limb leads"), then that individual is judged to have a positive 12-lead HF QRS ECG tracing for CAD or ACS, assuming that other potentially complicating conditions are not present simultaneously. Some of these other potentially complicating conditions include a QRS interval >120 ms, heart failure due either to cardiac systolic dysfunction (i.e., low ejection fraction) or diastolic dysfunction, left ventricular hypertrophy, atrial fibrillation, flutter or other atrial or ventricular arrhythmias, prior pacemaker insertion, and Wolff Parkinson White or other pre-excitation syndromes.

As shown in FIG. 20, individuals with $RAZ_N$s present in at least three contiguous precordial leads (e.g. V1-V3 or CR1-CR3 and similar combinations), or $RAZ_{AP}$s and/or $RAZ_K$s present in at least four contiguous precordial leads (e.g., V2-V5 or CR2-CR5 and similar combinations) are also judged to have a 12-lead HF QRS ECG tracing positive for CAD, assuming that no other potentially complicating conditions or factors are present. However, with respect to the detection of RAZs in the precordial leads, the 180° mirror of precordial lead V1 in the horizontal plane (i.e., a theoretical "minus V1" lead) may not be a positional equivalent of a theoretical V7 lead, and so RAZs in V6 and V1 (or in CR6 and CR1) may not be construed as contiguous for the purposes of 12-lead HF QRS diagnoses. Nonetheless, from FIG. 20, it should be apparent that RAZs in contiguous precordial leads V1-V3 may indicate posterior myocardial coronary insufficiency rather than (or in addition to) anterior myocardial coronary insufficiency, depending upon the specific clinical circumstances.

The following discussion pertains to situations in which $RAZ_{AP}$ and/or $RAZ_K$, when present in certain combinations of limb leads plus precordial leads, can constitute a positive test for CAD or ACS. When using conventional electrocardiography to evaluate patients with suspected ACS, it is known that ST segment elevation (and/or depression) in certain "precordial plus limb lead" combinations can be expected to occur when the infarction/ischemia is anatomically anterior versus posterior, inferior, lateral, "high lateral" etc., in location. Similarly, observations suggest that "precordial plus limb lead" patterns of changes also occur in the HF QRS ECG signals during myocardial ischmeia (i.e., morphologic RAZs develop in stereotypical lead locations that "match" with a specifically identified culprit vessel). For example, $RAZ_{AP}s$ have been observed in only leads II, III and aVF plus in leads V5-V6 in patients who have isolated right coronary artery obstructions, even when those patients have no simultaneous changes in their corresponding conventional ST segments. Patterned "limb plus precordial lead" changes such as these therefore also need to be recognized, even when the overall RAZ pattern that is present fails to simultaneously fulfill either the "three spatially contiguous $RAZ_Ns$" criterion or the "four spatially contiguous $RAZ_{AP}$ and/or $RAZ_K$" criterion. One easily-remembered "blanket" method for taking into account the most important of the possible "limb plus precordial" lead combinations suspicious for CAD or ACS is to simply accept, as "positive", any 12-lead HF QRS ECG tracing wherein a $RAZ_{AP}$ and/or a $RAZ_K$ is present in either "3 spatially contiguous limb leads plus 2 spatially contiguous precordial leads", and/or in "2 spatially contiguous limb leads plus 3 spatially contiguous precordial leads". Under this "blanket acceptance" rule, simple calculations reveal that there are a total of 54 such combinations possible whenever all 6 limb leads are used in combination with any singular set of 6 precordial leads. Specifically, recalling FIGS. 19A, 19B, and 20 above, the sub-criterion "3 spatially contiguous limb leads plus two spatially contiguous precordial leads" yields 30 different possible combinations, whereas the sub-criterion "2 spatially contiguous limb leads plus 3 spatially contiguous precordial leads" yields 24 different possible combinations, for a total of 54 different possible combinations. When thereafter using the 6 CR precordial leads in place of the 6 V precordial leads in a corresponding but separate set of analyses, another 54 such combinations become possible.

Some "limb plus precordial lead" combinations tend to occur more than others in patients with CAD and ACS. Thus, if one wants to increase test specificity, but possibly at the expense of test sensitivity, less inclusive sets of "limb plus precordial lead" combinations can be easily constructed and utilized, albeit clearly still within the spirit of the present invention. For example, one can construct a less inclusive set based upon common lead patterns of ST-segment change that encompass only those "limb plus precordial lead" combinations that most often occur in the conventional ECG during acute ischemia. Alternatively, another less inclusive set can be constructed on the basis of the most typical "limb plus precordial lead combinations" in which the HF QRS RMS voltage has been observed to change during ischemia, noting that RMS voltage is a measure of amplitude, whereas the RAZ and kurtosis measurements germane to present diagnostic criteria are measures of morphology, not amplitude. In short, any number of different subsets of "limb plus precordial lead" combinations can be derived and utilized as diagnostic criteria, and each of these could use any of the various types of RAZs defined herein and/or other measures of HF QRS morphology such as kurtosis, skewness, etc. However, any and all of these potential permutations are easily imagined and should be considered encompassed by the spirit of the present invention.

One specific example of a subset of "limb plus precordial lead" combinations that could be formulated to especially enhance the sensitivity and specificity of the 12-lead HF QRS ECG technique for detecting disease in the left circumflex coronary artery is shown below. This rather extensive example is given because even when severe, angiographic disease restricted to the left circumflex coronary artery has been historically difficult to diagnose using conventional ECG techniques alone.

In the discussion to follow, RCA refers to right coronary artery; LCx refers to left circumflex coronary artery; LAD refers to left anterior descending coronary artery; LMCA refers to left main coronary artery; D1 refers to first diagonal branch of LAD; and OM1 refers to first obtuse marginal branch of LCx.

Examples of allowed combinations (patterns) may be defined, but not restricted to:

"Inferior", "Right ventricular", "Posterior" and "Lateral" patterns:

$RAZ_{AP}$ and/or $RAZ_K$ or present in each of:
1) III, aVF, II, V5, V6 [e.g., RCA or LCx (inferior) or possibly LAD]
2) III, aVF, II, V1, V2 [e.g., RCA (right ventricular) or LCx (posterior/posterior-inferior)]
3) aVF, II, aVR, V1, V2 [e.g., potential variant of #2 above, especially if LCx]
4) aVL, I, aVR, V5, V6 [e.g., RCA or LCx—see especially reference (7)]
5) aVL, I, V4, V5, V6 [e.g., RCA, LCx (lateral) or possibly LAD]

"Anterior" and "Anterior High Lateral" patterns:

$RAZ_{AP}$ and/or $RAZ_K$ present in each of:
6) V2, V3, aVL, III, aVF (e.g., proximal LAD)
7) V2, V3, I, aVL, III (e.g., D1 branch of LAD; or possibly OM1 branch of LCx)

"Global" patterns due to LMCA disease or severe LAD disease:

$RAZ_{AP}$ and/or $RAZ_K$ present in each of:
8) I, aVR, II, V4, V5 (e.g., LMCA or LAD)
9) I, aVR, II, V5, V6 (e.g., LMCA or LAD)
10) aVR, II, V4, V5, V6 (e.g., LMCA or LAD)
11) I, aVR, V4, V5, V6 (e.g., LMCA or LAD)

Other patterns may be devised to yield diagnostically useful results within the scope and spirit of the invention.

Another easily imagined permutation of the diagnostic criteria allows for positive overall test results on the basis of having five or more spatially contiguous "Abboud" RAZs, and/or "limb plus precordial lead" combinations of Abboud RAZs occurring in six or more leads. Although it is generally not an issue for RAZs of the N or AP type, the significance of any single Abboud (A) RAZ can nonetheless be quite debatable at times, particularly in the limb leads, where the overall RMS voltages tend to be smaller than in the central precordial leads. This is shown in respect of FIG. 21.

Figure 21:
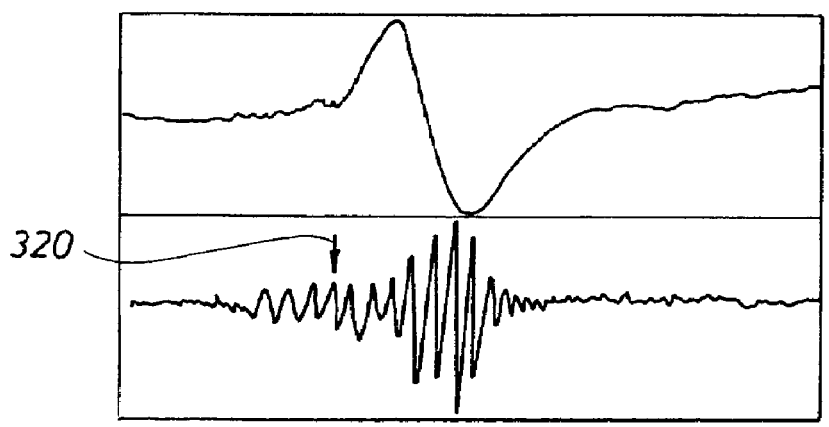
FIG. 21 is a time plot of low and high frequencies in an ECG signal.

FIG. 21 illustrates an HF QRS signal from lead aVF with a $RAZ_A$ that might be of questionable clinical significance. The $RAZ_A$ of questionable significance is present near the beginning of the QRS interval. An arrow 320 indicates the secondary local maximum defining the $RAZ_A$. This $RAZ_A$ should be compared to FIG. 16B, in which the RAZ in clearly significant. The $RAZ_A$ in the case of FIG. 21 is of "questionable" significance because there is very little difference between the absolute amplitude of the envelope sample point (secondary local maximum) that defines it and the absolute amplitudes of the envelope sample points that are immediately adjacent to that secondary local maximum. A decision with respect to the legitimacy versus the illegitimacy of a $RAZ_A$ like this is best left to a visually astute and experienced clinician who also takes into consideration the characteristics of the HF QRS signals in contiguous leads II, III etc. However, "automatic diagnosis" decisions related to Abboud or other types of RAZs can be legitimized to some extent by taking into simultaneous consideration the given patient's cardiac axis.

For example, one permutation considers a 12-lead HF QRS ECG test "positive" for CAD or some other cardiac condition only when a previously defined type of RAZ is present in X contiguous leads (and/or in the combination of X plus Y contiguous limb+precordial leads) and when it is present in both of those limb (or precordial) leads that are nearest to the given patient's cardiac axis in the frontal (or horizontal) plane. Imagine, for example, that one planned to use "5 spatially contiguous $RAZ_A$" as part of one's criteria for a positive overall test for some cardiac condition. Further imagine that a $RAZ_A$ was indeed present in all of a given patient's limb leads except lead II, and at the same time the patient's cardiac frontal plane axis was +70 degrees based on the conventional ECG. If the criteria have been permuted so as to contain the additional "axis requirement" as noted above for the frontal plane, then such a patient would actually not have an overall positive test in this case because with a cardiac frontal plane axis of +70 degrees, he/she would need to have a $RAZ_A$ in both leads II and aVF (i.e., in the two leads whose territory is most adjacent to +70 degrees) to fulfill the permuted criteria. In other words, neither of these two leads could be that single lead of the six limb leads that is "missing" the $RAZ_A$, and which turns out to be the case in this particular example.

Similarly, when using the "4 spatially contiguous $RAZ_{AP}$ and/or $RAZ_K$" criterion permuted with the additional "axis requirement" as noted above, a patient with a cardiac frontal plane axis of +10 degrees would need to have a $RAZ_{AP}$ and/or $RAZ_K$ specifically present in both leads I and aVR, in addition to having such RAZs present in at least 2 of the other immediately adjacent limb leads, in order to have a positive overall test for CAD, etc. In a patient that has a frontal plane cardiac axis of "exactly" −30, 0, 30, 60, 90 or 120 degrees, then only that single limb lead that points to that exact cardiac frontal plane axis (i.e., and not a second adjacent lead as well) might be required to be among those containing the given required RAZ in order to constitute a positive overall test.

These stated examples represent just a few of the many possible permutations within the spirit of the present invention that could be generated by utilizing cardiac axis in combination with RAZ presence/absence in order to formulate slightly variant sets of criteria for diagnoses of cardiac conditions, including CAD. Besides combining RAZ presence/absence with cardiac axes, RAZ presence/absence could also be combined with any number of other objective cardiac measures (such as QRS, QT, RR, PR or other electrophysiologic intervals, variability or dispersion of these same intervals, cardiac ejection fractions, stroke volumes, tracer uptakes, etc.) and/or with patient features (such as height, weight, body mass index, hip/waist/torso measurements, various laboratory values, etc.), in order to generate even more variant sets of criteria for cardiac diagnoses, and all of these easily foreseeable permutations should too be considered to fall within the spirit of the present invention.

Functional Operation

As previously described regarding FIGS. 4 and 5, when all hardware components are appropriately connected and the patient or subject is attached to the device, natural electrical signals from the subject's heart are first sensed by the standard ECG electrodes 12 located on the skin of the chest at the conventional 12-lead (i.e., 10 electrode) positions. After processing in accordance with the logic shown in FIG. 21, the RAZ detectors for each lead 72 provide signals to the component 300 for display. In relationship to the present invention, the displays depicted in FIGS. 22 and 23 are representative graphics material in addition to that shown and described above.

Figure 22:
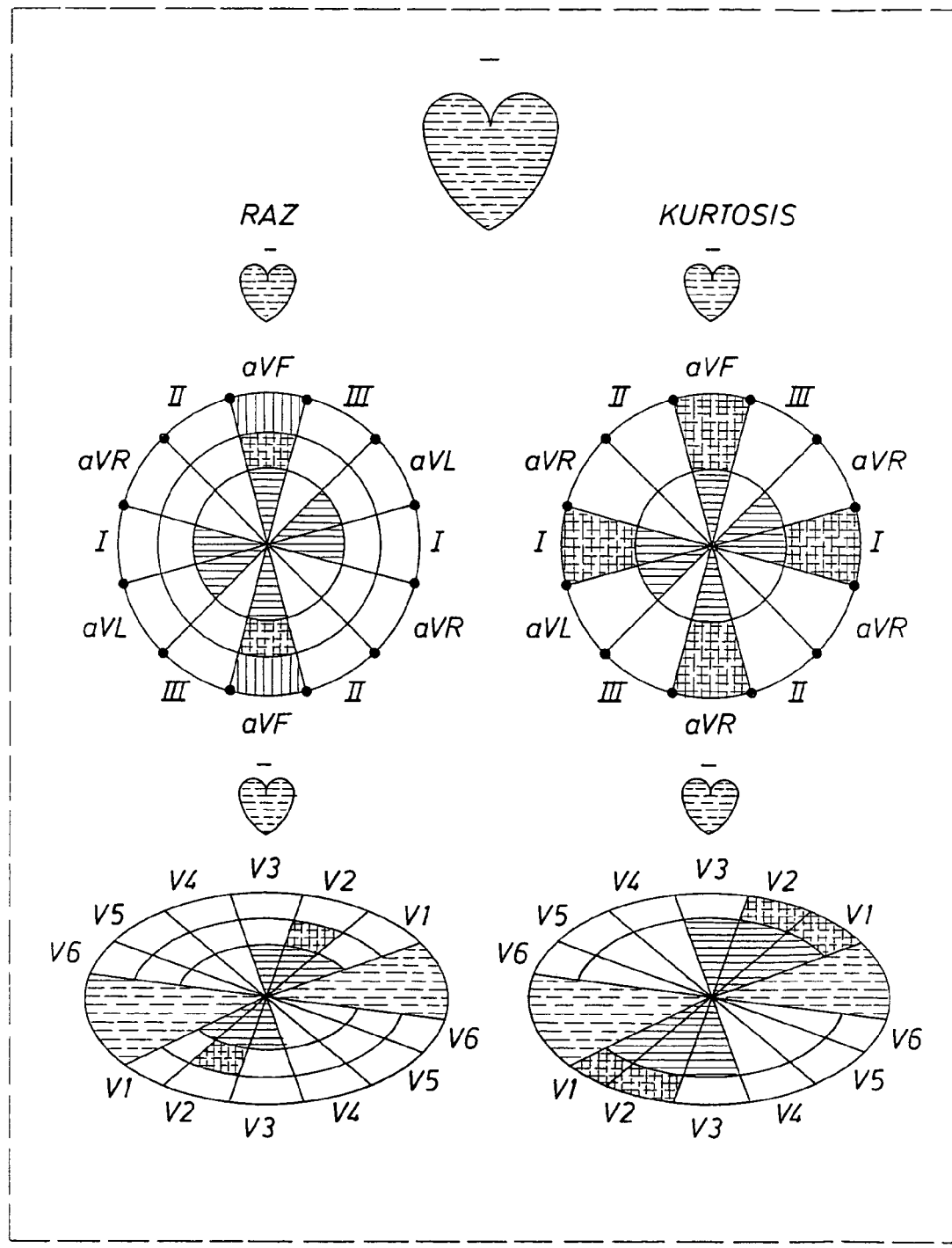
FIG. 22 is an illustration of output displays of the present invention.

FIG. 22 illustrates an HF QRS ECG user interface "Automatic Diagnosis Panel" that takes advantage of the 12-lead HF QRS criteria for diagnosis of CAD or ACS just described. In the figure, vertical lines indicate the color red, horizontal lines indicate gray, cross-hatching indicates yellow, and darkened areas indicate blue. In the specific case depicted, the patient's overall test is "positive" (i.e., suspicious for CAD in this case), as indicated by the large red heart with the "+" sign above it in the upper center portion of the figure. Of the 4 individual diagrams (in addition to the large red heart) that constitute FIG. 22, only the limb lead RAZ diagram (upper left) has a small red heart with a "+" sign immediately above it, whereas the other three individual diagrams have small gray hearts with "−" signs above them, indicating their individually negative status. The upper left hand diagram (i.e., the limb lead RAZ diagram) is positive in this case because it is showing the simultaneous presence of a $RAZ_N$ in each of the three contiguous limb leads II, aVF and III, as indicated by the outermost (red) shading in those leads. If any one of the four individual diagrams is positive, or, for the $RAZ_{AP}$ and $RAZ_K$ (both indicated by yellow shading when present), if combinational diagrams (i.e., limb+limb or precordial+precordial or limb+precordial) are positive for a "diagnostic combination" (the latter is also the case here because $RAZ_{AP}$ and $RAZ_K$ combined are also present in the accepted combination of leads II, aVF, III, V5 and V6, as outlined in the text), then by definition, the entire test is positive, and the large heart becomes red and "+". In the present case, the precordial RAZ diagram (lower left) is by itself negative because it does not reveal 3 contiguous $RAZ_N$ (i.e., only lead V6 has a $RAZ_N$), nor four contiguous $RAZ_{AP}$ (only leads V5 and V6 have $RAZ_{AP}$). Similarly, both the limb lead and the precordial lead kurtosis diagrams (right side of figure) are negative by themselves in this case because neither of these diagrams shows the presence of four contiguous $RAZ_K$. Note that the innermost (blue) shading represents the presence of a $RAZ_A$ (in the RAZ diagrams) and the presence of a "gray zone" level of kurtosis (in the kurtosis diagrams).

Figure 23:
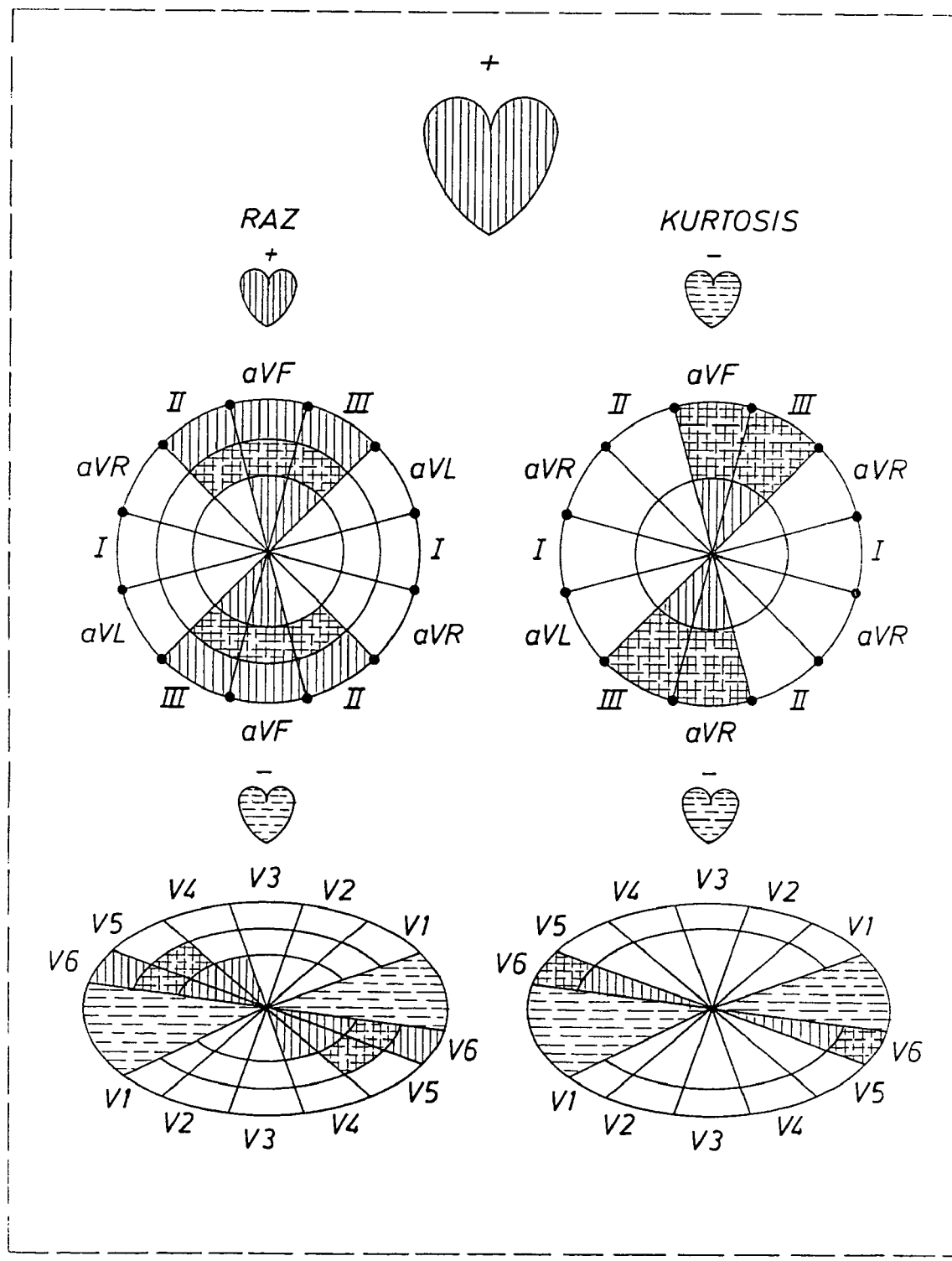
FIG. 23 is an illustration of output displays of the present invention.

FIG. 23 illustrates an HF QRS user interface "Automatic Diagnosis Panel" that depicts an overall negative test for CAD, as indicated by the large gray heart with the "−" sign above it in the upper center portion of the figures. This patient's test is overall negative because all four diagrams are individually negative, and also because there are no positive "$RAZ_{AP}$/$RAZ_K$ combinations" present. The upper left hand diagram (i.e., the limb lead RAZ diagram) is negative because it does not reveal 3 contiguous $RAZ_N$[a $RAZ_N$ is present only in limb lead aVF, outermost (red) shading] nor four contiguous $RAZ_{AP}$ [a $RAZ_{AP}$ is present only in limb lead aVF, middle-layer (yellow) shading]. The precordial RAZ diagram (lower left) is likewise negative because it does not reveal 3 contiguous $RAZ_N$ (i.e., no precordial lead has a $RAZ_N$), nor four contiguous $RAZ_{AP}$ [only precordial lead V2 has a $RAZ_{AP}$, middle-layer (yellow) shading]. Similarly, both the limb lead and the precordial lead kurtosis diagrams (right side of figure) are again negative in this case because neither of those diagrams shows the presence of four contiguous $RAZ_K$ [outermost (yellow) shading]. Combining the $RAZ_{AP}$ and/or the $RAZ_K$ that are present across the limb leads or across the precordial leads also does not lead to a "four contiguous RAZ" phenomoneon, nor are there any combinations of such RAZs present in the allowed configurations of "3 contiguous limb leads+2 contiguous precordial leads" or "2 contiguous limb+3 contiguous precordial leads".

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

We claim:

1. An electrocardiograph system comprising:
   means for sensing a plurality of electrocardiograph signals, the signals comprising cardiac data and a succession of waves;
   means for independently identifying the QRS complex in each wave;
   means for signal-averaging the QRS complex in each wave;
   means for band-pass filtering the signal-averaged QRS complex in a high frequency range thereby deriving high frequency components of the QRS complex, wherein the means for band-pass filtering passes frequencies from 150 Hz to 250 Hz;
   means for detecting a reduced amplitude zone within the high frequency components of the QRS complex in each wave relating to cardiac function, the reduced amplitude zone within the high frequency components of the QRS complex comprising RAZ data;
   means for relating at least three of the detected reduced amplitude zones in accordance with predetermined criteria to develop cardiac diagnoses; and
   means for displaying the cardiac and RAZ data in real time on a monitor.

2. The system of claim 1, wherein the reduced amplitude zone is defined as a region within the high frequency components of the QRS complex lying between two neighboring maxima or minima.

3. The system of claim 1, wherein the reduced amplitude zone is defined as a region within the high frequency components of the QRS complex lying between two neighboring maxima or minima, and wherein a second, smaller local maximum or minimum within the high frequency components of the QRS complex is at least a certain user-selectable percentage of the larger of the maxima or minima.

4. The system of claim 3, wherein the percentage is any percentage between 0% and 100%.

5. The system of claim 1, wherein the reduced amplitude zone is defined as a region within the high frequency components of the QRS complex lying between two neighboring maxima or minima, and wherein the voltage of a second, smaller local maximum within the high frequency components of the QRS complex is at least a certain user-selectable percentage of that of the larger of the maxima or wherein the voltage of a second, smaller local minimum within the high frequency components of the QRS complex is at least a certain user-selectable percentage of that of the larger of the minima.

6. The system of claim 1, further comprising means for analyzing a kurtosis of the high frequency components of the QRS complex and determining the kurtosis below a predetermined minimum.

7. The system of claim 1, wherein the means for sensing a plurality of electrocardiograph signals comprise a plurality of electrodes, and wherein the electrodes are defined in spatial relation to one another.

8. The system of claim 7, wherein the means for relating at least three of the detected reduced amplitude zones, relate the reduced amplitude zones in terms of spatial relation.

9. The system of claim 7, wherein the means for relating includes means for relating all of the detected reduced amplitude zones from the means for detecting.

10. The system of claim 1, further comprising:
    means for recording a first set of baseline cardiac and RAZ data; and
    means for comparing the first set of baseline cardiac and RAZ data with cardiac and RAZ data captured in real time.

11. The system of claim 10, wherein the means for displaying the cardiac data and the RAZ data in real-time on a monitor includes means for displaying the first set of baseline cardiac and RAZ data along with cardiac and RAZ data captured in real time.

12. The system of claim 1, wherein the means for sensing a plurality of electrocardiograph signals includes CR precordial leads.

13. The system of claim 1, wherein the means for signal-averaging is comprised of:
    means for developing a time-varying, signal-averaged template based on the QRS complex in each wave from each of the means of sensing;
    means for cross-correlating the QRS complex in each wave in real time from each of the means of sensing with a respective time-varying, signal-averaged template; and
    means for accepting or rejecting each QRS complex in each wave based on the means for cross-correlating, wherein accepted QRS complexes are incorporated into the time-varying, signal-averaged template.

14. The system of claim 13 further comprising:
    means for recording data, wherein the data are comprised of the signals; the time-varying, signal-averaged template; the RAZ data; or any combination; and
    means for indicating likely coronary artery disease, acute coronary syndrome, or other cardiac condition from the recorded data when a reduced amplitude zone is present in each of three or more sensing means, wherein the sensing means are spatially contiguous.

15. The system of claim 13,
    wherein the reduced amplitude zone is comprised of an Abboud RAZ, Abboud Percent RAZ, a NASA RAZ, Kurtosis RAZ, or any combination, and
    wherein the predetermined criteria are comprised of a predetermined percentage occurrence of the Abboud RAZ, Abboud Percent RAZ, NASA RAZ, Kurtosis RAZ, or any combination within a predetermined number of the accepted QRS complexes from at least one of the plurality of electrocardiograph signals.

16. The system of claim 13,
    wherein the reduced amplitude zone is comprised of an Abboud RAZ, Abboud Percent RAZ, a NASA RAZ, Kurtosis RAZ, or any combination, and
    wherein the predetermined criteria are comprised of an occurrence of the Abboud RAZ, Abboud Percent RAZ, NASA RAZ, Kurtosis RAZ, or any combination when derived from the final time-varying, signal-averaged template.

* * * * *